US008871929B2

(12) United States Patent
Chan et al.

(10) Patent No.: US 8,871,929 B2
(45) Date of Patent: Oct. 28, 2014

(54) FUSED-IMIDAZOYL COMPOUNDS USEFUL AS ANTIMICROBIAL AGENTS

(75) Inventors: Tin-Yau Chan, Edison, NJ (US); Henry M. Vaccaro, South Plainfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/813,482

(22) PCT Filed: Jul. 28, 2011

(86) PCT No.: PCT/US2011/045637
§ 371 (c)(1),
(2), (4) Date: Mar. 15, 2013

(87) PCT Pub. No.: WO2012/018662
PCT Pub. Date: Feb. 9, 2012

(65) Prior Publication Data
US 2013/0210816 A1    Aug. 15, 2013

Related U.S. Application Data

(60) Provisional application No. 61/370,156, filed on Aug. 3, 2010.

(51) Int. Cl.
| C07D 409/00 | (2006.01) |
| C07D 471/00 | (2006.01) |
| C07D 401/00 | (2006.01) |
| C07D 513/02 | (2006.01) |
| A61K 31/50 | (2006.01) |
| A61K 31/497 | (2006.01) |
| A61K 31/44 | (2006.01) |
| C07D 471/04 | (2006.01) |
| C07D 487/04 | (2006.01) |

(52) U.S. Cl.
CPC ............ *C07D 471/04* (2013.01); *C07D 487/04* (2013.01)
USPC ........... 544/331; 544/350; 544/362; 546/121; 514/249; 514/253.04; 514/300

(58) Field of Classification Search
USPC ............. 514/249, 253.04, 300; 544/331, 350, 544/362; 546/121
See application file for complete search history.

(56) References Cited

U.S. PATENT DOCUMENTS

| 2008/0188515 A1 | 8/2008 | Thormann |
| 2008/0287453 A1 | 11/2008 | Bower et al. |
| 2009/0275577 A1 | 11/2009 | Sciotti et al. |
| 2010/0105721 A1 | 4/2010 | Lee et al. |

FOREIGN PATENT DOCUMENTS

| WO | WO 2008016648 A2 * | 2/2008 |
| WO | WO2008/150089 A1 | 12/2008 |

OTHER PUBLICATIONS

Bienayme, H. et al., Angew. Chem. Int. Ed. vol. 37, pp. 2234-2237. Published 1998.*
Bienayme, H. et al. Angew Chem Int. Ed. vol. 37, pp. 2234-2237. Published 1998.*
Bienayme et al, (Angew Chem. Int. Ed., vol. 37 pp. 2234-2237. Published 1998).*

* cited by examiner

*Primary Examiner* — Paul Zarek
*Assistant Examiner* — George W Kosturko
(74) *Attorney, Agent, or Firm* — Sheldon O. Heber; Henry P. Wu

(57) ABSTRACT

The invention relates to fused-imidazoyl compounds of Formula (I): wherein ring A, $R^1$, $R^2$, $R^3$, $R^4$, $R^5$, $R^6$, $R^7$, $R^8$, $R^9$, m and n are as defined herein. Also disclosed are pharmaceutical compositions containing the compound of Formula (I) and methods of using the compound of Formula (I) to treat microbial infections.

Formula I

11 Claims, No Drawings

FUSED-IMIDAZOYL COMPOUNDS USEFUL AS ANTIMICROBIAL AGENTS

This application is a 371 National Stage Application of PCT/US2011/045637 with an international filing date of Jul. 28, 2011 and claims the benefit of U.S. Provisional Patent Application No. 61/370,156 filed Aug. 3, 2010, each of which is hereby incorporated by reference in its entirety.

FIELD OF THE INVENTION

The present invention relates to fused-imidazolyl compounds, pharmaceutical compositions containing them, and their use as antimicrobial agents.

BACKGROUND OF THE INVENTION

Resistance to antibiotics is a growing medical concern as infections caused by resistant organisms are difficult to treat. Resistance is particularly problematic among bacterial pathogens such as *Enterococcus faecium*, *Staphylococcus aureus*, *Mycobacterium tuberculosis*, *Pseudomonas aeruginosa*, *Klebsiella pneumoniae*, and *Acinetobacter baumannii* where resistance to multiple antibiotics is often observed. Consequently, there is a need to develop new antibiotics to treat infections caused by drug resistant microbes.

SUMMARY OF THE INVENTION

The compounds of this invention, and pharmaceutically acceptable compositions thereof, are antimicrobials. These compounds are represented by the structural Formula I:

Formula I or a pharmaceutically acceptable salt, solvate, hydrate, ester, prodrug or stereoisomer thereof,
wherein:
X is selected from the group consisting of
(a) CH, and
(b) N;
Y is selected from the group consisting of:
(a) CH, and
(b) N;
ring A is selected from the group consisting of:
(a) cycloalkyl,
(b) cycloalkenyl,
(c) aryl,
(d) heterocyclyl,
(e) heterocyclenyl,
(f) heteroaryl,
wherein said cycloalkyl, cycloalkenyl, aryl, heterocyclyl, heterocyclenyl, and heteroaryl is unsubstituted or substituted by at least one (preferably 1 to 3) $R^2$, wherein when each of said cycloalkyl, cycloalkenyl, aryl, heterocyclyl, heterocyclenyl, and heteroaryl, has substituents on adjacent carbon atoms, said substituents can optionally be taken together with the carbon atoms to which they are attached to form a five- or six-membered cycloalkyl, cycloalkenyl, heterocyclyl, heterocyclenyl, aryl or heteroaryl,
wherein said five- or six-membered cycloalkyl, cycloalkenyl, heterocyclyl, aryl or heteroaryl is unsubstituted or substituted by at least one (preferably 1 to 3) $R^2$;

each $R^1$ is independently selected from the group consisting of:
(a) halo,
(b) alkyl,
(c) alkoxyl,
(d) —CN,
(e) —NH$_2$,
(f) —N(alkyl)$_2$,
(g) —N(H)alkyl, and
(h) haloalkyl;

each $R^2$ is independently selected from the group consisting of:
(a) alkyl,
(b) alkoxyl,
(c) haloalkyl,
(d) alkenyl,
(e) alkynyl,
(f) —NH$_2$,
(g) —N(alkyl)$_2$,
(h) —N(H)alkyl,
(i) halogen,
(j) —CN,
(k) —OH, and
(l) heterocyclyl;

$R^3$ is selected from the group consisting of:
(a) aryl,
(b) heteroaryl, and
(c) heteroaryl-N-oxide,
wherein each of said aryl, heteroaryl, or heteroaryl-N-oxide is independently unsubstituted or substituted with one or more substituents independently selected from the group consisting of alkyl, haloalkyl, alkoxyl, thioalkoxyl, NO$_2$, halo and —CN;

$R^{1a}$ and $R^{4b}$ are independently selected from the group consisting of:
(a) hydrogen,
(b) alkyl, and
(c) haloalkyl;

$R^{5a}$, $R^{5b}$, $R^{6a}$, $R^{6b}$, $R^{7a}$, $R^{7b}$, $R^{8a}$ and $R^{8b}$ are independently selected from the group consisting of:
(a) hydrogen,
(b) alkyl, and
(c) haloalkyl;

$R^9$ is selected from the group consisting of:
(a) hydrogen,
(b) alkyl, and
(e) haloalkyl; and
m and n independently are 0, 1, 2, 3 or 4,
with the proviso that when Y is N, and Ring A is phenyl, $R^3$ is not

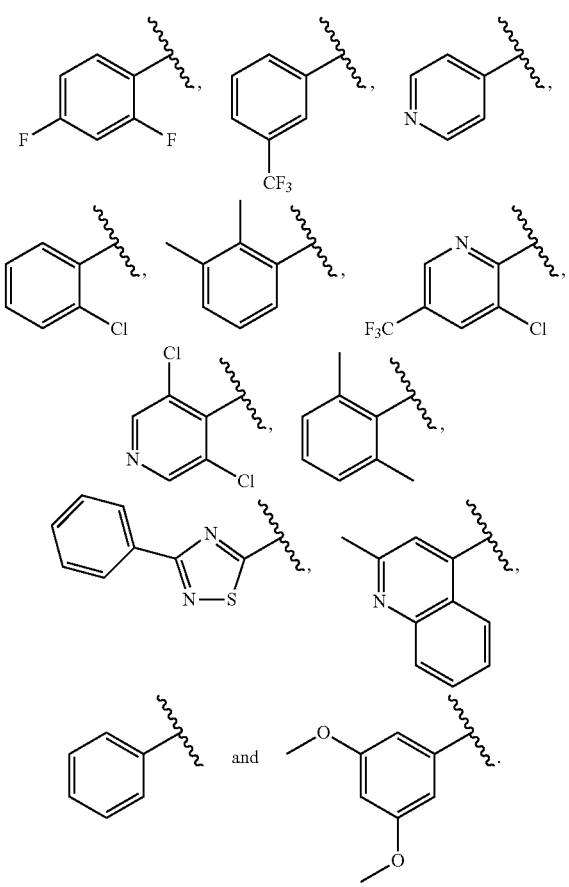

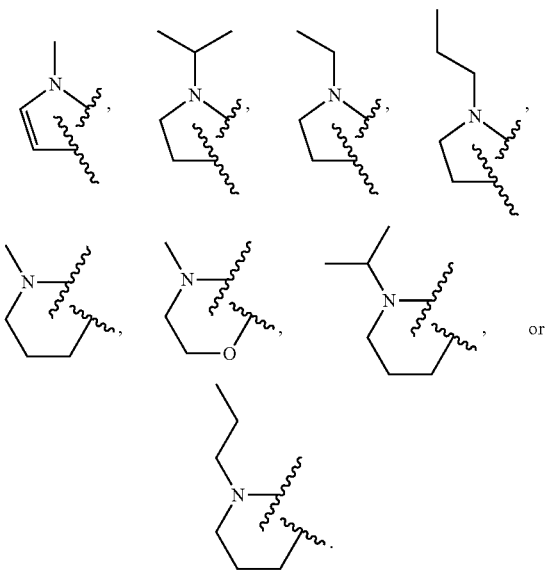

The present invention provides pharmaceutical compositions comprising said compounds, or a pharmaceutically acceptable salt, solvate, hydrate, ester, prodrug or stereoisomer thereof.

The present invention also provides methods of treating microbial infections, comprising administering to a patient in need of such treatment at least one compound of Formula I, or a pharmaceutically acceptable salt, solvate, hydrate, ester, prodrug or stereoisomer thereof.

DETAILED DESCRIPTION

In another embodiment in Formula I, X is CH.
In yet another embodiment in Formula I, X is N.
In another embodiment in Formula I, Y is CH.
In yet embodiment in Formula I, Y is N.
In yet another embodiment in Formula I, X is CH; and Y is N.
In another embodiment in Formula I, X is CH; and Y is CH.
In one embodiment in Formula I, X is N; and Y is N.
In another embodiment in Formula I, X is N; and Y is CH.
In another embodiment in Formula I, ring A is selected from the group consisting of:
(a) cycloalkyl,
(b) cycloalkenyl,
(c) aryl,
(d) heterocyclyl,
(e) heterocyclenyl,
(f) heteroaryl,
  wherein said cycloalkyl, cycloalkenyl, aryl, heterocyclyl, heterocyclenyl, and heteroaryl is unsubstituted or substituted by at least one (preferably 1 to 3) $R^2$,
  wherein when each of said cycloalkyl, cycloalkenyl, aryl, heterocyclyl, heterocyclenyl, and heteroaryl, has two $R^2$ substituents on adjacent carbon atoms, said substituents can optionally be taken together with the carbon atoms to which they are attached to form:

In yet another embodiment in Formula I, ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
  wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$.

In another embodiment in Formula I, each $R^1$ is independently selected from the group consisting of:
(a) fluoro,
(b) chloro,
(c) —$CO_2$methyl
(d) —$CF_3$, and
(e) —$CH_3$.

In another embodiment in Formula I, each $R^2$ is independently selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl.

In another embodiment in Formula I, $R^3$ is selected from the group consisting of

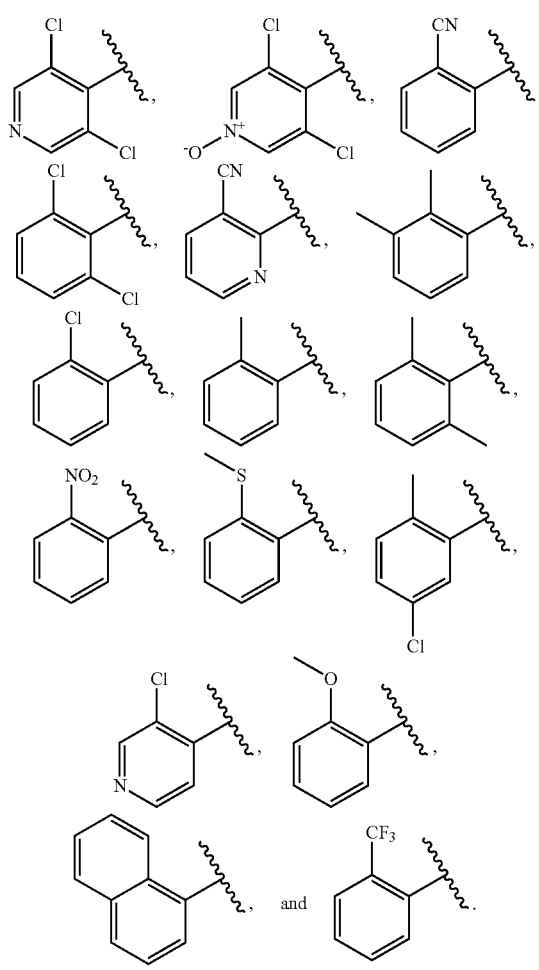

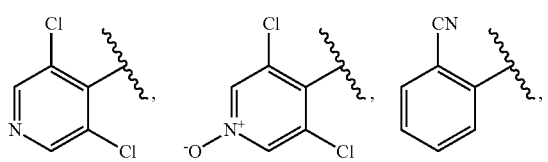

In another embodiment in Formula I, ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
  wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$; and
$R^3$ is selected from the group consisting of

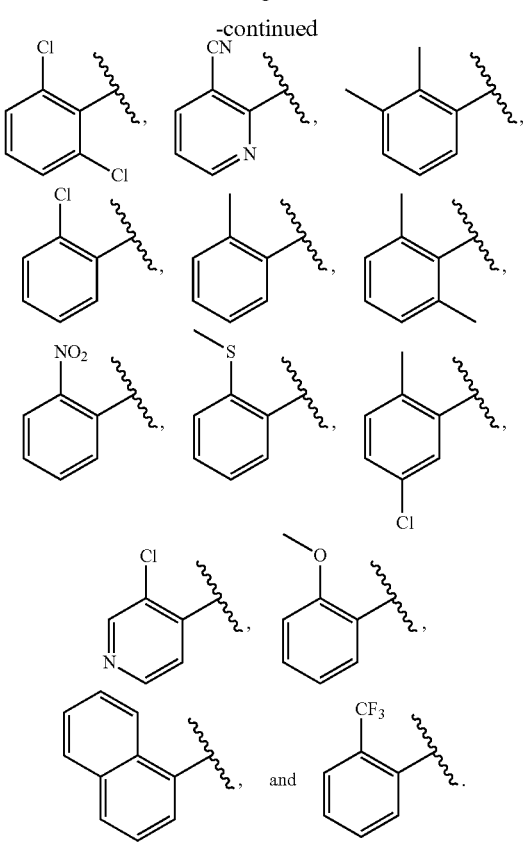

In another embodiment in Formula I, X is N;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
  wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$; and
$R^3$ is selected from the group consisting of:

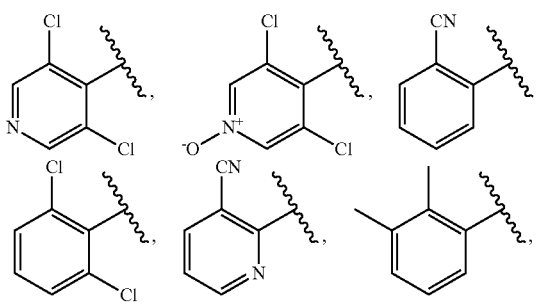

-continued

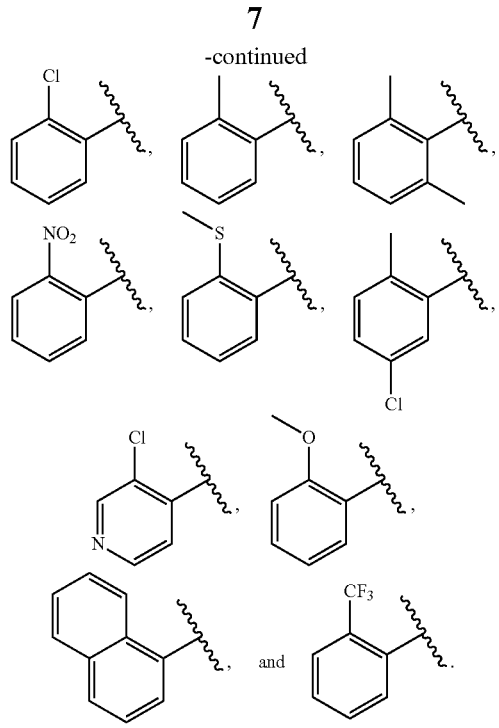

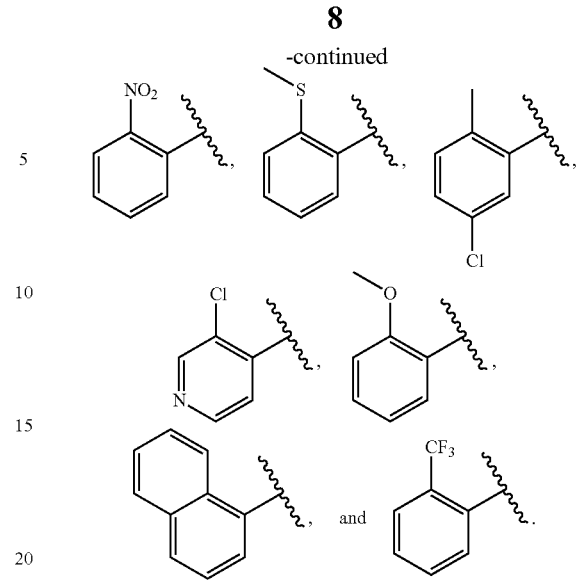

In another embodiment in Formula I, X is CH;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
  wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$; and
$R^3$ is selected from the group consisting of

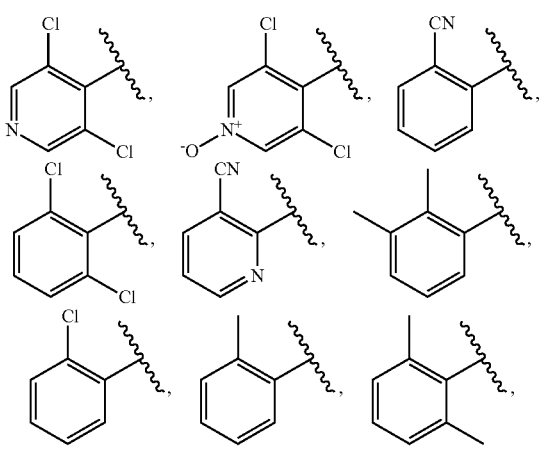

In another embodiment in Formula I, $R^{4a}$ and $R^{4b}$ are each hydrogen.

In one embodiment in Formula I, $R^{5a}$, $R^{5b}$, $R^{6a}$, $R^{6b}$, $R^{7a}$, $R^{7b}$, $R^{8a}$ and $R^{5b}$ are each hydrogen.

In another embodiment in Formula I, $R^9$ is hydrogen.

In one embodiment in Formula I, $R^{4a}$ and $R^{4b}$ are each hydrogen; and
$R^{5a}$, $R^{5b}$, $R^{6a}$, $R^{6b}$, $R^{7a}$, $R^{7b}$, $R^{8a}$ and $R^{8b}$ are each hydrogen.

In another embodiment in Formula I, X is N;
$R^{4a}$ and $R^{4b}$ are each hydrogen; and
$R^{5a}$, $R^{5b}$, $R^{6a}$, $R^{6b}$, $R^{7a}$, $R^{7b}$, $R^{8a}$ and $R^{8b}$ are each hydrogen.

In another embodiment in Formula I, X is N;
Y is CH;
$R^{4a}$ and $R^{4b}$ are each hydrogen; and
$R^{5a}$, $R^{5b}$, $R^{6a}$, $R^{6b}$, $R^{7a}$, $R^{7b}$, $R^{8a}$ and $R^{8b}$ are each hydrogen.

In another embodiment in Formula I, X is N;
Y is N;
$R^{4a}$ and $R^{4b}$ are each hydrogen; and
$R^5$, $R^{5b}$, $R^{6a}$, $R^{6b}$, $R^{7a}$, $R^{7b}$, $R^{8a}$ and $R^{8b}$ are each hydrogen.

In another embodiment in Formula I, X is N;
Y is CH;
$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is N;
Y is N;
$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
$R^{4a}$ and $R^{4b}$ are each hydrogen; and
$R^{5a}$, $R^{5b}$, $R^{6a}$, $R^{6b}$, $R^{7a}$, $R^{7b}$, $R^{8a}$ and $R^{8b}$ are each hydrogen.

In another embodiment in Formula I, X is CH;
Y is CH;
$R^{4a}$ and $R^{4b}$ is hydrogen; and
$R^{5a}$, $R^{5b}$, $R^{6a}$, $R^{6b}$, $R^{7a}$, $R^{7b}$, $R^{8a}$ and $R^{8b}$ are each hydrogen.

In another embodiment in Formula I, X is CH;
Y is N;

$R^{4a}$ and $R^{4b}$ are each hydrogen; and
$R^{5a}$, $R^{5b}$, $R^{6a}$, $R^{6b}$, $R^{7a}$, $R^{7b}$, $R^{8a}$ and $R^{8b}$ are each hydrogen.

In another embodiment in Formula I, X is CH;
Y is CH;
$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
Y is N;
$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is N;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
 wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(c) —$CO_2$methyl
(d) —$CF_3$, and
(e) —$CH_3$;
each $R^2$ is independently selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is N;
Y is CH;
ring A is selected from the group consisting of
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
 wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(c) —$CO_2$methyl
(d) —$CF_3$, and
(e) —$CH_3$;
each $R^2$ is selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^{4a}$ and $R^{4b}$ are each hydrogen;
$R^{5a}$, $R^{5b}$, $R^{6a}$, $R^{7a}$, $R^{7b}$, $R^{8a}$ and $R^{8b}$ are each hydrogen; and
$R^9$ is hydrogen.

In another embodiment in Formula I, X is N;
Y is N;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
 wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(c) —$CO_2$methyl
(d) —$CF_3$, and
(e) —$CH_3$;
each $R^2$ is selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^{4a}$ and $R^{4b}$ are each hydrogen;
$R^{5a}$, $R^{5b}$, $R^{6a}$, $R^{6b}$), $R^{7a}$, $R^{7b}$, $R^{8a}$ and $R^{8b}$ are each hydrogen; and
$R^9$ is hydrogen.

In another embodiment in Formula I, X is CH;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and (i) furanyl,
wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(c) —$CO_2$methyl
(d) —$CF_3$, and
(e) —$CH_3$;
each $R^2$ is selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
Y is CH;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(e) —$CO_2$methyl
(d) —$CF_3$, and
(e) —$CH_3$;
each $R^2$ is selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^{4a}$ and $R^{4b}$ are each hydrogen;
$R^{5a}$, $R^{5b}$, $R^{6a}$, $R^{6b}$, $R^{7a}$, $R^{7b}$,
$R^{8a}$ and $R^{8b}$ are each hydrogen; and
$R^9$ is hydrogen.

In another embodiment in Formula I, X is CH;
Y is N;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(c) —$CO_2$methyl
(d) —$CF_3$, and
(e) —$CH_3$;
each $R^2$ is selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^{4a}$ and e are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is N;
each $R^1$ is independently selected from the group consisting of:
(a) fluoro,
(b) chloro,
(c) —$CO_2$methyl
(d) —$CF_3$, and
(e) —$CH_3$;
each $R^2$ is selected from the group consisting of
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^3$ is selected from the group consisting of

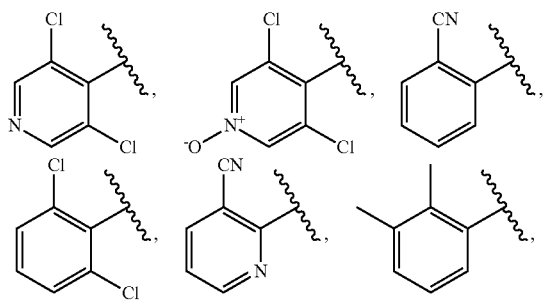

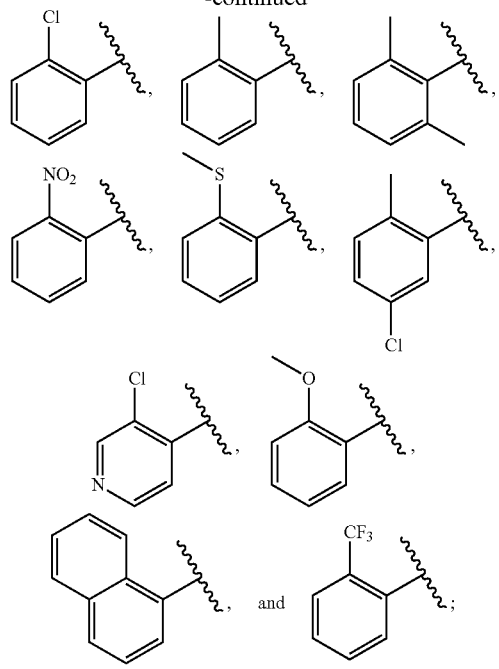

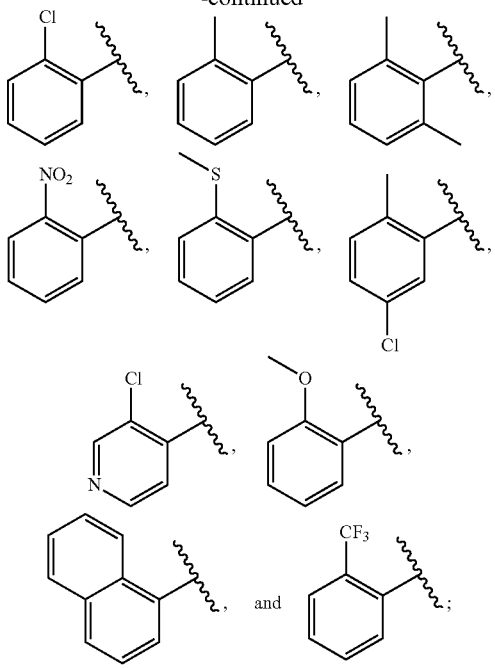

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is N;
Y is CH;
each $R^1$ is independently selected from the group consisting of:
(a) fluoro,
(b) chloro,
(c) —CO$_2$methyl
(d) —CF$_3$, and
(e) —CH$_3$;
each $R^2$ is selected from the group consisting of:
(a) methyl,
(b) ethyl,
(c) propyl,
(d) isopropyl,
(e) —N(CH$_3$)$_2$,
(f) pyrrolidinyl,
(g) piperidinyl,
(h) thiomorpholinyl, and
(i) morpholinyl;
$R^3$ is selected from the group consisting of

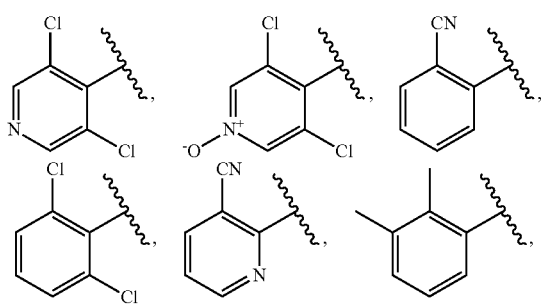

$R^{4a}$ and $R^{4b}$ are each hydrogen;
$R^{5a}$, $R^{5b}$, $R^{6A}$, $R^{6b}$, $R^{7a}$, $R^{7b}$, $R^{8a}$ and $R^{8b}$ are each hydrogen; and
$R^9$ is hydrogen.

In another embodiment in Formula I, X is N;
Y is N;
each R' is independently selected from the group consisting of
(a) fluoro,
(b) chloro,
(c) —CO$_2$methyl
(d) —CF$_3$, and
(e) —CH$_3$;
each $R^2$ is selected from the group consisting of:
(a) methyl,
(b) ethyl,
(c) propyl,
(d) isopropyl,
(e) —N(CH$_3$)$_2$,
(f) pyrrolidinyl,
(g) piperidinyl,
(h) thiomorpholinyl, and
(i) morpholinyl;
$R^3$ is selected from the group consisting of

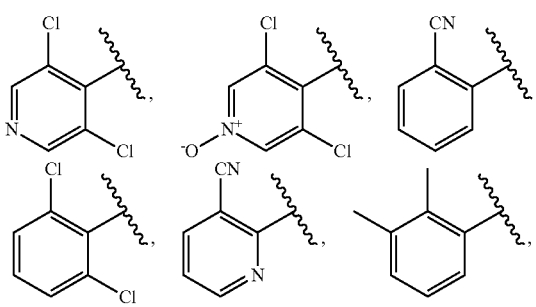

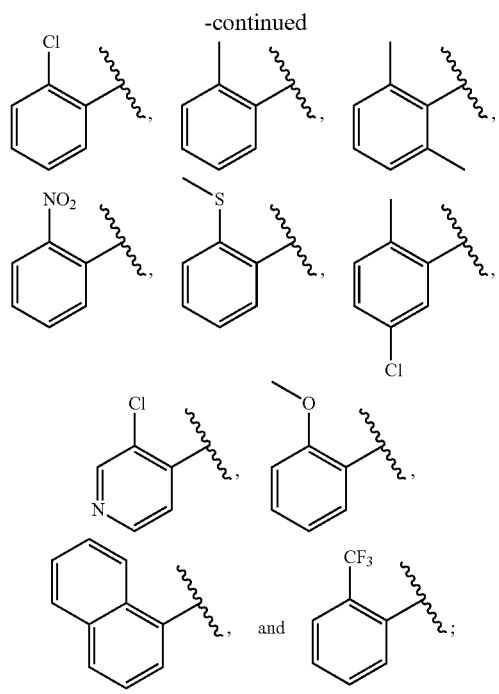

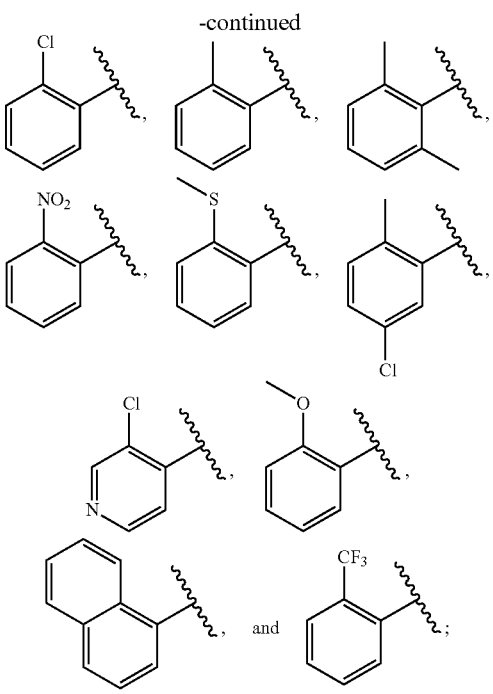

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
each $R^1$ is independently selected from the group consisting of:
(a) fluoro,
(b) chloro,
(c) —CO$_2$methyl
(d) —CF$_3$, and
(e) —CH$_3$;

each $R^2$ is selected from the group consisting of:
(a) hydrogen,
(b) methyl,
(c) ethyl,
(d) propyl,
(e) isopropyl,
(f) —N(CH$_3$)$_2$,
(g) pyrrolidinyl,
(h) piperidinyl,
(i) thiomorpholinyl, and
(j) morpholinyl;

$R^3$ is selected from the group consisting of

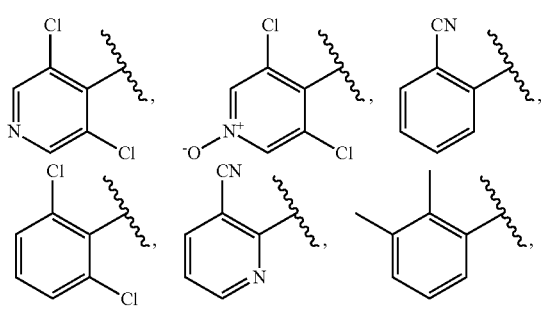

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
Y is CH;
each $R^1$ is independently selected from the group consisting of:
(a) fluoro,
(b) chloro,
(e) —CO$_2$methyl
(d) —CF$_3$, and
(e) —CH$_3$;

each $R^2$ is selected from the group consisting of:
(a) methyl,
(b) ethyl,
(c) propyl,
(d) isopropyl,
(e) —N(CH$_3$)$_2$,
(f) pyrrolidinyl,
(g) piperidinyl,
(h) thiomorpholinyl, and
(i) morpholinyl;

$R^3$ is selected from the group consisting of

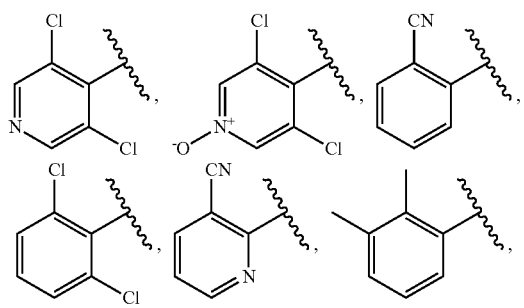

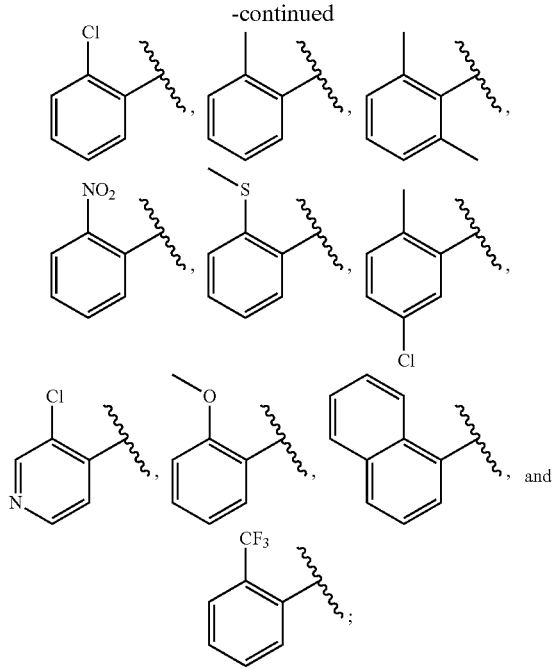

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
Y is N;
each $R^1$ is independently selected from the group consisting of:
(a) fluoro,
(b) chloro,
(c) —CO$_2$methyl
(d) —CF$_3$, and
(e) —CH$_3$;
each $R^2$ is selected from the group consisting of:
(a) methyl,
(b) ethyl,
(c) propyl,
(d) isopropyl,
(e) —N(CH$_3$)$_2$,
(f) pyrrolidinyl,
(g) piperidinyl,
(h) thiomorpholinyl, and
(i) morpholinyl;
$R^3$ is selected from the group consisting of

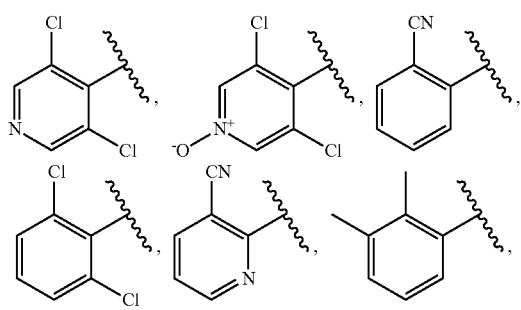

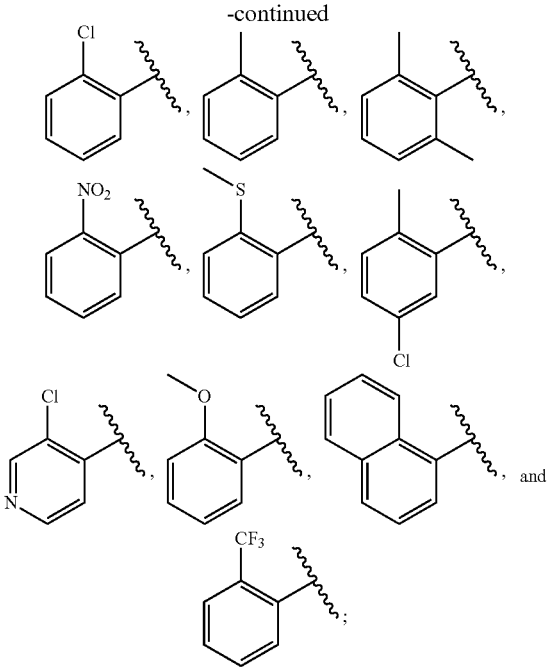

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is N;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
  (j) wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(e) —CO$_2$CH$_3$
(d) —CF$_3$, and
(e) —CH$_3$;
each $R^2$ is selected from the group consisting of:
(a) methyl,
(b) ethyl,
(c) propyl,
(d) isopropyl,
(e) —N(CH$_3$)$_2$,
(f) pyrrolidinyl,
(g) piperidinyl,
(h) thiomorpholinyl, and
(i) morpholinyl;
$R^3$ is selected from the group consisting of

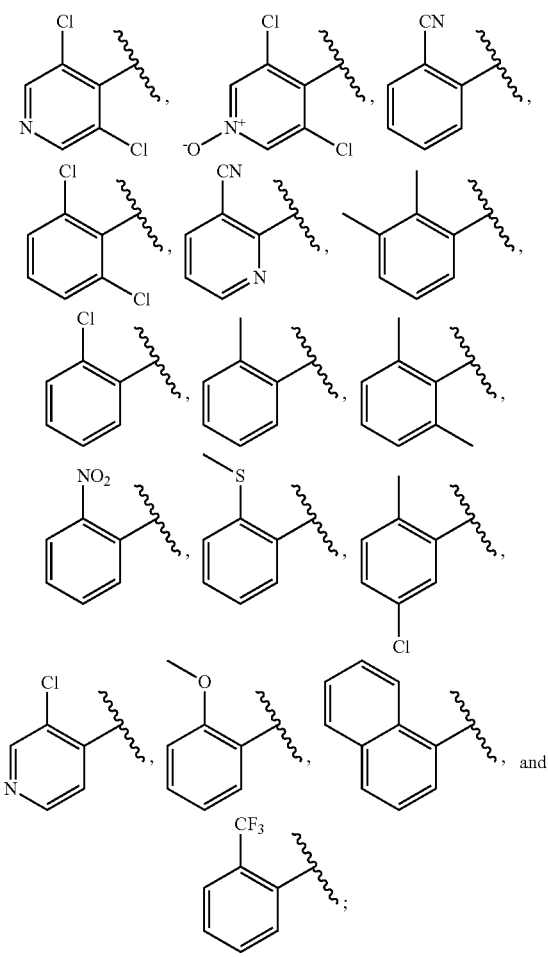

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.
In another embodiment in Formula I, X is N;
Y is CH;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;
each $R^1$ is independently selected from the group consisting of:
(a) fluoro,
(b) chloro,
(c) —$CO_2CH_3$
(d) —$CF_3$, and
(e) —$CH_3$;
each $R^2$ is selected from the group consisting of:
(a) methyl,
(b) ethyl,
(c) propyl,
(d) isopropyl,
(e) —$N(CH_3)_2$,
(f) pyrrolidinyl,
(g) piperidinyl,
(h) thiomorpholinyl, and
(i) morpholinyl;
$R^3$ is selected from the group consisting of

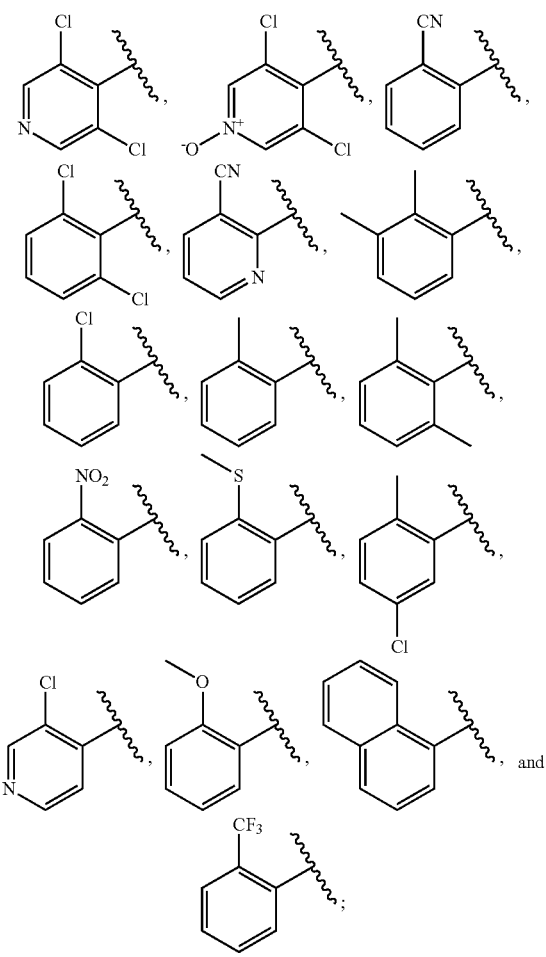

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.
In another embodiment in Formula I, X is N;
Y is N;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) R²;
each R¹ is independently selected from the group consisting of:
(a) fluoro,
(b) chloro,
(c) —CO₂CH₃,
(d) —CF₃, and
(e) —CH₃;
each R² is selected from the group consisting of:
(a) methyl,
(b) ethyl,
(c) propyl,
(d) isopropyl,
(e) —N(CF₁₃)₂,
(f) pyrrolidinyl,
(g) piperidinyl,
(h) thiomorpholinyl, and
(i) morpholinyl;
R³ is selected from the group consisting of

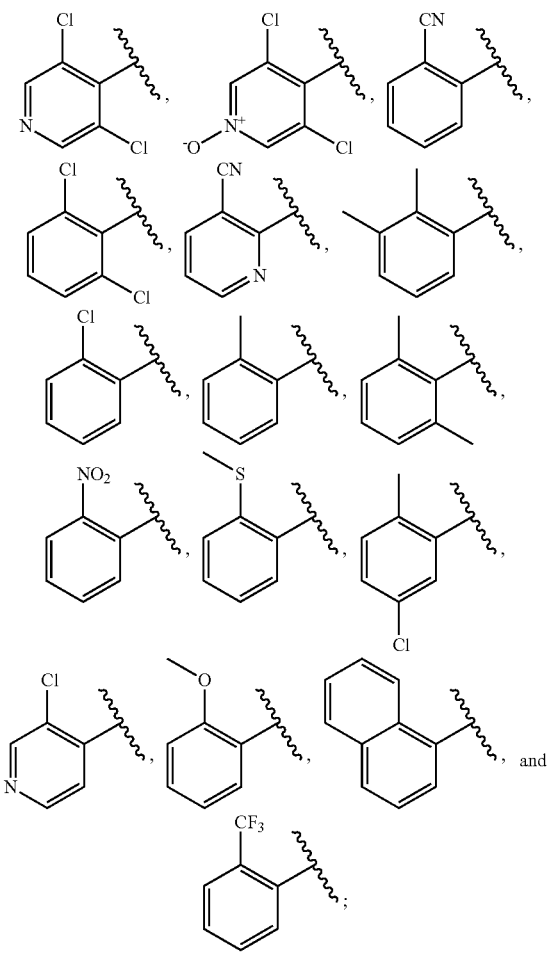

R⁴ᵃ and R⁴ᵇ are each hydrogen;
R⁵ᵃ, R⁵ᵇ, R⁶ᵃ, R⁶ᵇ, R⁷ᵃ, R⁷ᵇ, R⁸ᵃ and R⁸ᵇ are each hydrogen; and
R⁹ is hydrogen.
In another embodiment in Formula I, X is CH;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
   wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) R²;
each R¹ is independently selected from the group consisting of:
(a) fluoro,
(b) chloro,
(c) —CO₂CH₃,
(d) —CF₃, and
(e) —CH₃;
each R² is selected from the group consisting of
(a) methyl,
(b) ethyl,
(c) propyl,
(d) isopropyl,
(e) —N(CH₃)₂,
(f) pyrrolidinyl,
(g) piperidinyl,
(h) thiomorpholinyl, and
(i) morpholinyl;
R³ is selected from the group consisting of

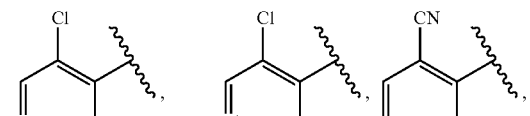

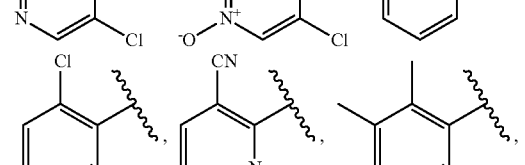

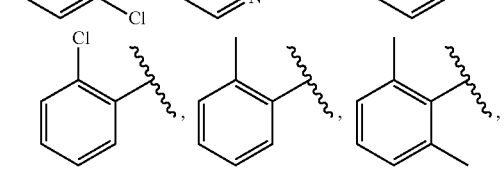

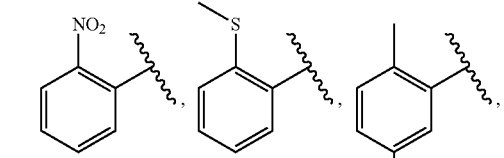

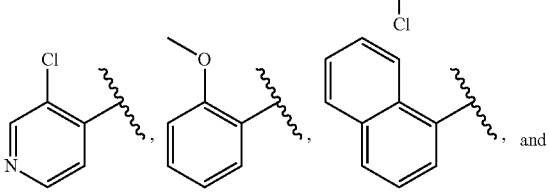

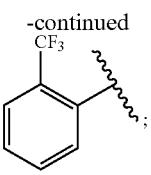

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
Y is CH;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;

each $R^1$ is independently selected from the group consisting of:
(a) fluoro,
(b) chloro,
(c) —CO$_2$CH$_3$
(d) —CF$_3$, and
(e) —CH$_3$;

each $R^2$ is selected from the group consisting of:
(a) methyl,
(b) ethyl,
(c) propyl,
(d) isopropyl,
(e) —N(CH$_3$)$_2$,
(f) pyrrolidinyl,
(g) piperidinyl,
(h) thiomorpholinyl, and
(i) morpholinyl;

$R^3$ is selected from the group consisting of

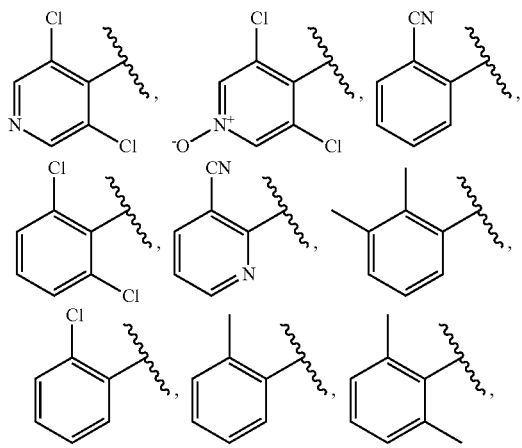

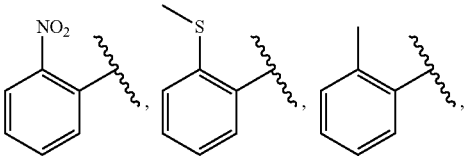

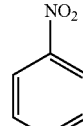

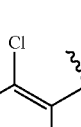

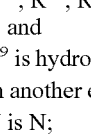

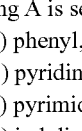

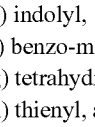

$R^{4a}$ and $R^{4b}$ are each hydrogen;
$R^{5a}$, $R^{5b}$, $R^{6a}$, $R^{6b}$, $R^{7a}$, $R^{7b}$, $R^{8a}$ and $R^{8b}$ are each hydrogen; and
$R^9$ is hydrogen.

In another embodiment in Formula I, X is CH;
Y is N;
ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
wherein said phenyl, pyridinyl, pyrimidinyl, indolinyl, indolyl, benzo-morpholinyl, tetrahydroquinolinyl, thienyl, and furanyl is unsubstituted or substituted by at least one (preferably 1 to 3) $R^2$;

each R' is independently selected from the group consisting of:
(a) fluoro,
(b) chloro,
(c) —CO$_2$CH$_3$
(d) —CF$_3$, and
(e) —CH$_3$;

each $R^2$ is selected from the group consisting of:
(a) methyl,
(b) ethyl,
(c) propyl,
(d) isopropyl,
(e) —N(CH$_3$)$_2$,
(f) pyrrolidinyl,
(g) piperidinyl,
(h) thiomorpholinyl, and
(i) morpholinyl;

$R^3$ is selected from the group consisting of

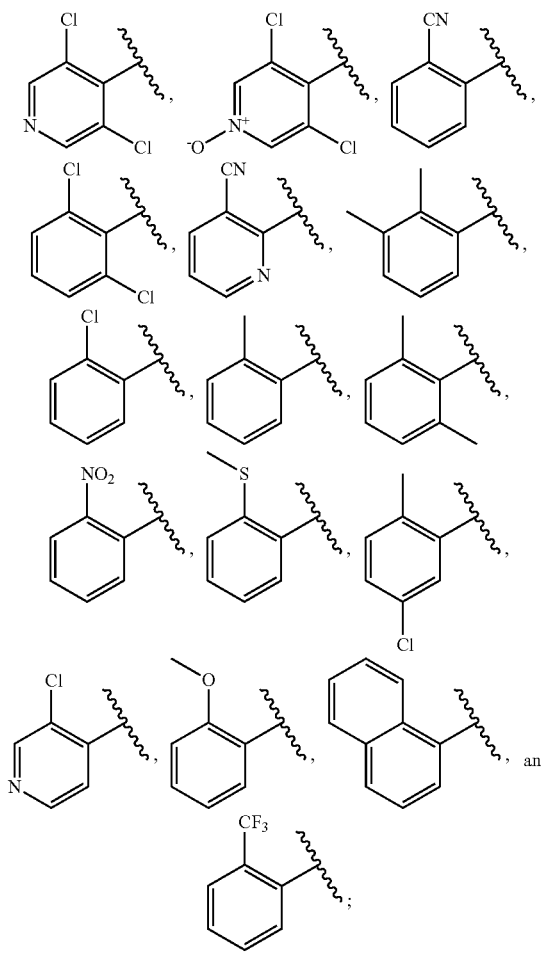

$R^{4a}$ and $R^{4b}$ are each hydrogen;

$R^{5a}$, $R^{5b}$, $R^{6a}$, $R^{6b}$, $R^{7a}$, $R^{7b}$, $R^{8a}$ and $R^{8b}$ are each hydrogen; and $R^9$ is hydrogen.

In one embodiment, the compounds of the present invention include those of Formula I-a:

Formula I-a

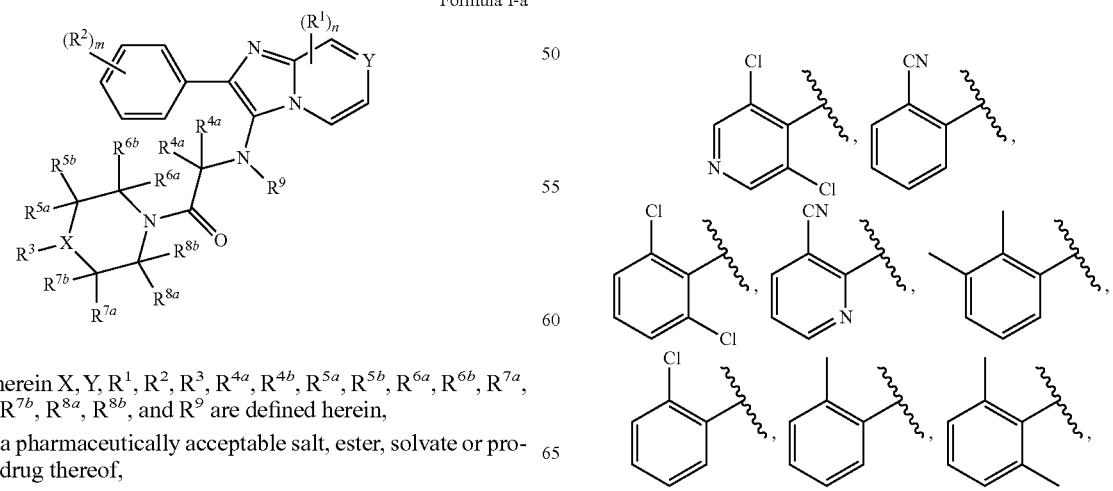

wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof, with the proviso that when Y is N, $R^3$ is not

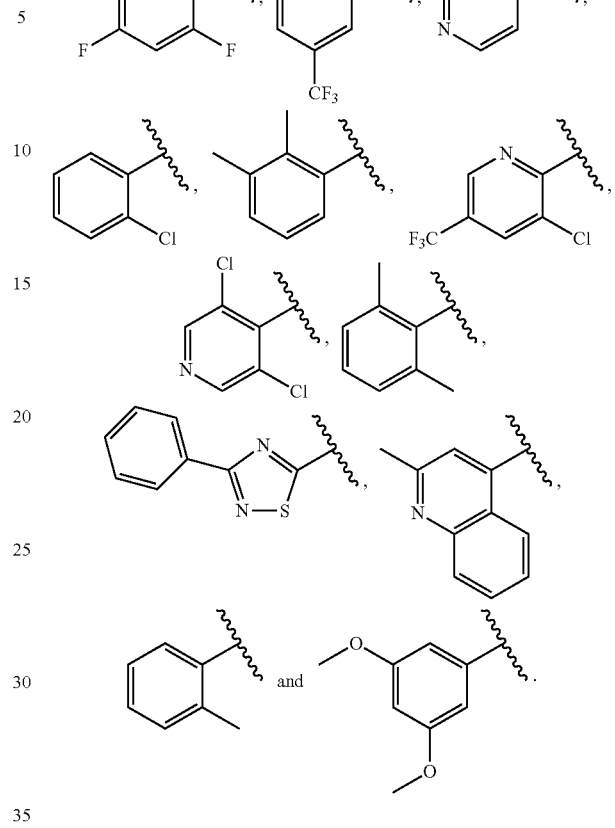

In another embodiment, the compounds of the present invention include those of Formula I-a, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-a, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is selected from the group consisting of -continued

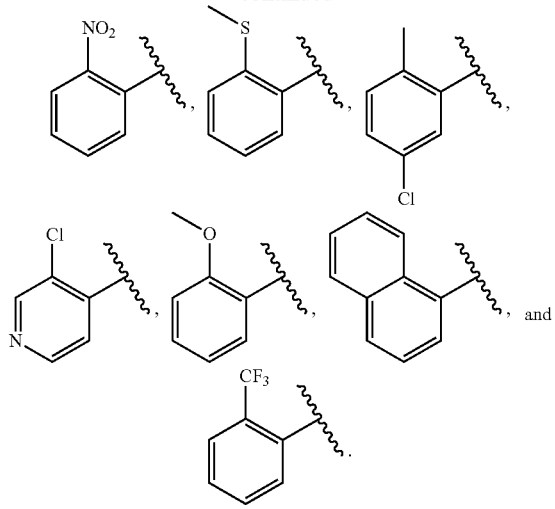

In one embodiment, the compounds of the present invention include those of Formula I-b:

Formula I-b

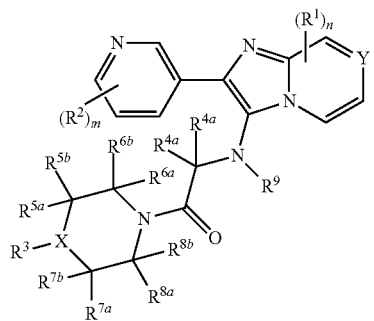

wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof.

In another embodiment, the compounds of the present invention include those of Formula I-b, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof, In yet another embodiment, the compounds of the present invention include those of Formula I-b, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is selected from the group consisting of

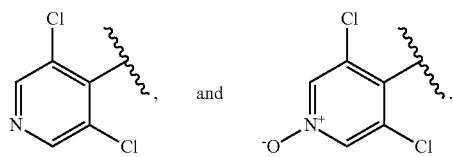

In one embodiment, the compounds of the present invention include those of Formula I-c:

Formula I-c

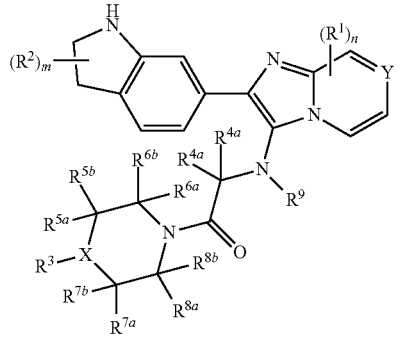

wherein X, Y, $R^1$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof.

In another embodiment, the compounds of the present invention include those of Formula I-c, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-c, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is selected from the group consisting of

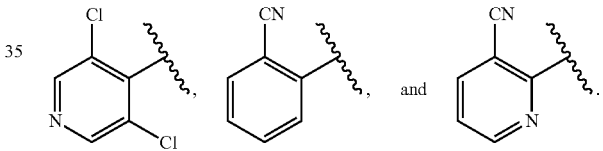

In one embodiment, the compounds of the present invention include those of Formula I-d:

Formula I-d

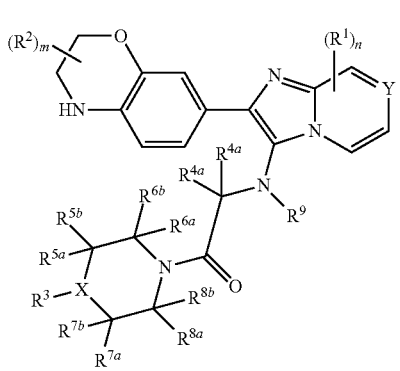

wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof.

In another embodiment, the compounds of the present invention include those of Formula I-d, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-d, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is

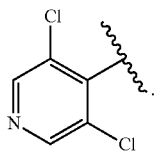 [SMILES: *c1c(Cl)cncc1Cl]

In one embodiment, the compounds of the present invention include those of Formula I-e:

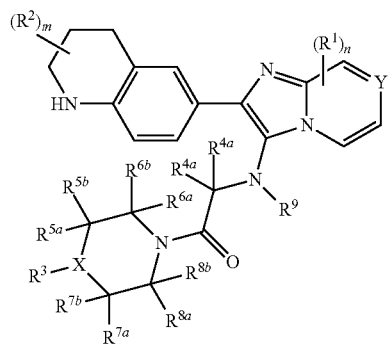

Formula I-e wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof.

In another embodiment, the compounds of the present invention include those of Formula I-e, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-e, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is selected from the group consisting of

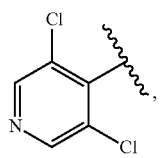 and 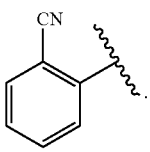

In one embodiment, the compounds of the present invention include those of Formula I-f:

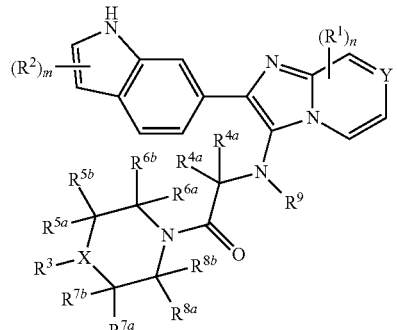

Formula I-f wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester solvate or prodrug thereof.

In another embodiment, the compounds of the present invention include those of Formula I-f, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-f, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is

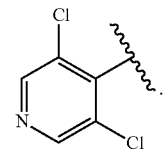 [SMILES: *c1c(Cl)cncc1Cl]

In one embodiment, the compounds of the present invention include those of Formula I-g:

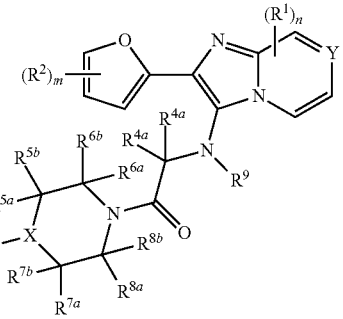

Formula I-g wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof.

In another embodiment, the compounds of the present invention include those of Formula I-g, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-g, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is

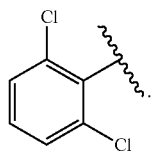 [SMILES: *c1c(Cl)cccc1Cl]

In one embodiment, the compounds of the present invention include those of Formula I-h:

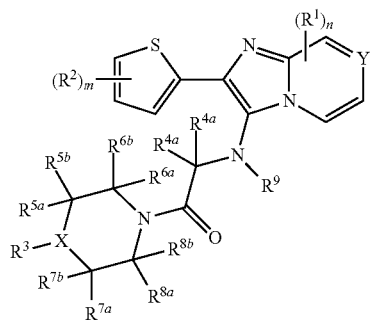

Formula I-h wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof.

In another embodiment, the compounds of the present invention include those of Formula I-h, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-h, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is selected from the group consisting of

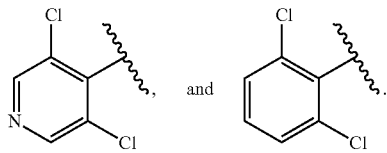 [SMILES: *c1c(Cl)cncc1Cl ; *c1c(Cl)cccc1Cl]

In one embodiment, the compounds of the present invention include those of Formula I-i:

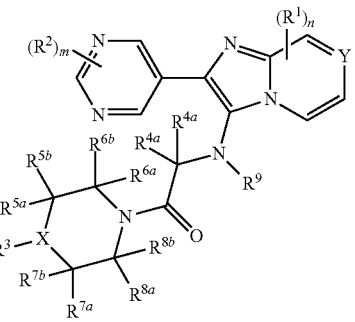

Formula I-i wherein X, Y, $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are defined herein, or a pharmaceutically acceptable salt, ester, solvate or prodrug thereof.

In another embodiment, the compounds of the present invention include those of Formula I-i, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen, or a pharmaceutically acceptable salt, ester, solvate or prodrug thereof.

In yet another embodiment, the compounds of the present invention include those of Formula I-i, wherein $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, and $R^9$ are independently hydrogen; and $R^3$ is

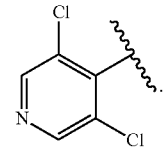

In another embodiment, the compound of Formula I is selected from those disclosed in Table 1, or a pharmaceutically acceptable salt, solveate or ester thereof.

In one embodiment, the present invention provides an isolated or purified form of a compound of Formula I, or a pharmaceutically acceptable salt, solvate or ester thereof.

In another embodiment, the present invention provides a compound of Formula I, at least 90% pure.

In another embodiment, the present invention provides a compound of Formula I, at least 95% pure.

In yet another embodiment, the present invention provides a compound of Formula I, at least 99% pure.

In another embodiment, the present invention provides a pharmaceutical composition comprising a therapeutically effective amount of at least one compound of any of Formula I, or a pharmaceutically acceptable salt or ester thereof, in combination with a pharmaceutically acceptable carrier.

In yet another embodiment, the present invention provides a pharmaceutical composition, further comprising one or more compounds selected from the group consisting of an antibiotic, an anti-inflammatory agent, a matrix metalloprotease inhibitor, a lipoxygenase inhibitor, a cytokine antagonist, an immunosuppressant, an anti-cancer agent, an antiviral agent, a cytokine, a growth factor, an immunomodulator, a prostaglandin, an anti-vascular hyperproliferation compound, and an agent which increases the susceptibility of bacterial organisms to antibiotics.

In one embodiment, the present invention is used for treating a microbial infection, comprising administering to a patient in need of such treatment at least one compound of Formula I, or a pharmaceutically acceptable salt, solvate, hydrate, ester, prodrug or stereoisomer thereof.

In one embodiment, the microbial infection is a bacterial or fungal infection.

In one embodiment, the microbial infection is a bacterial infection.

In one embodiment, the microbial infection is a fungal infection.

In another embodiment, the bacterial infection is caused by a drug-resistant bacterium.

In another embodiment, the bacterial infection is caused by a gram-negative bacterium.

In yet another embodiment, the bacterial infection is caused by a gram-positive bacterium.

In one embodiment, the bacterial infection is caused by at least one gram-negative organism selected from the group consisting of *Acinetobacter* spp., *Actinobacillus* spp., *Aeromonas* spp., *Alcaligenes* spp., *Bacteroides* spp., *Bartonella* spp., *Bordetella* spp., *Branhamella* spp., *Brucella* spp., *Burkholderia* spp., *Campylobacter* spp., *Citrobacter* spp., *Coxiella* spp., *Edwarsiella* spp., *Ehrlichia* spp., *Eikenella* spp., *Enterobacter* spp., *Escherichia* spp., *Flavobacterium* spp., *Francisella* spp., *Fusobacterium* spp., *Haemophilus* spp., *Haemophilus* spp., *Helicobacter* spp., *Kingella* spp., *Klebsiella* spp., *Legionella* spp., *Moraxella* spp., *Morganella* spp., *Neisseria* spp., *Pasteurella* spp., *Plesiomonas* spp., *Porphyromonas* spp., *Prevotella* spp., *Prevotella* spp., *Prevotella* spp., *Proteus* spp., *Providencia* spp., *Pseudomonas* spp., *Ricketsia* spp., *Salmonella* spp., *Serratia* spp., *Shigella* spp., *Stenotrophomonas* spp., *Streptobacillus* spp, *Vibrio* spp. and *Yersinia* spp.

In another embodiment, the bacterial infection is caused by at least one grain-negative organism selected from the group consisting of *Acinetobacter baumannii, Pseudomonas aeruginosa, Escherichia coli, Neisseria gonorrhoeae* and *Chlamydia trachomatis*.

In one embodiment, the bacterial infection is caused by at least one gram-positive organism selected from the group consisting of *Bacillus* spp., *Listeria* spp., *Staphylococcus* spp., *Enterococcus* spp., *Clostridium* spp., *Streptococcus* spp., *Actinomyces* spp. and *Mycobacterium* spp.

In another embodiment, the bacterial infection is caused by at least one gram-positive organism selected from the group consisting of *Staphylococcus aureus, Streptococcus pyogenes, Streptococcus pneumoniae, Clostridium difficile, Enterococcus Faecalis*, and *Enterococcus faecium.*

In yet one embodiment, the bacterial infection is caused by *Staphylococcus aureus.*

In one embodiment, the bacterial infection is selected from one or more of the following: urinary tract infection, a respiratory infection, a surgical wound infection, a central line infection, bacteremia, bronchitis, sinusitis, pneumonia, prostatitis, a skin or soft tissue infection, an intra-abdominal infection, or a bacterial infection of febrile neutropenic patients.

In one embodiment, the method further comprises the administration of one or more compounds selected from the group consisting of an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, and an anti-vascular hyperproliferation compound, either as part of a multiple dosage form together with said compound or as a separate dosage form.

In multiple dosage form a compound of Formula I is administered separately with an agent described above, and in a single dosage form, a compound of Formula I is combined an agent described above is administered in a single composition.

Non-limiting examples of classes of antibiotics suitable for administration with the compounds of the present invention, and compositions thereof, include quinolones, beta-lactams, macrolides, glycopeptides, and lipopetides.

Non-limiting examples of specific antibiotics include alatrofloxacin, altrofloxacin, amdinocillin, amoxicillin, ampicillin, azithromycin, bacampicillin, besifloxacin, carbenicillin, ceadroxil, cefaclor, cefazolin, cefditoren, cefinir, cefixime, cefprozil, ceftibuten, cefuroxime axetil, cephapirin, chloramphenicol, chlortetracycline, ciprofloxacin, cloxacillin, clarithromycin, clavulanate potassium, clindamycin phosphate, cloxacillin, cyclacillin, dactinomycin, daptomycin, dicloxacillin, dirithromycin, doxycycline, enoxacin, erythromycin, fosfomycin tromethamine, fluorometholone, gatifloxacin, gemifloxacin, gentamicin, grepafloxacin, hetacillin, kanamycin, levofloxacin, lincomycin, linezolid, lomefloxacin, maxaquin, mezlocillin, minocycline, moxifloxacin, mupirocin, nafcillin, netilmicin, norfloxacin, ofloxacin, oxacillin, oxytetracycline, penicillamine, penicillin G, penicillin V, piperacillin, plicamycin, rifamycin, rifabutin, rifampin, rifapentine, rifaximin, soarfloxacin, sparfloxacin, sulfamethoxazole, sulfisoxazole acetyl, telithromycin, ticarcillin, tobramycin, trimethoprim, troleandomycin, trovafloxacin, vancomycin, viomycin, and mixtures thereof.

In another embodiment, the method further comprises the step of administering to said patient an agent that increases the susceptibility of bacterial organisms to antibiotics.

Agents that increase the susceptibility of bacteria to antibiotics are known. A number of patents such as U.S. Pat. Nos. 5,523,288, 5,783,561 and 6,140,306 describe permeability-increasing bactericidal proteins that increase the bacterial susceptibility to antibiotics. Other agents that increase the susceptibility of bacteria to antibiotics have been described in the literature. (Vaara, *Microbiological Reviews,* 56, 395-411 (1992); Tsubery, et al., *J. Med. Chem.* 43, 3085-3092 (2000)).

As used above, and throughout this disclosure, the following terms, unless otherwise indicated, shall be understood to have the following meanings: "At least one" compound of formula I means 1, 2, 3 or 4 different compounds, but preferably one compound of formula I is used in the claimed methods. Similarly, when "at least one" is used in connection with the additional agents used in the combinations, 1, 2, 3 or 4 additional agents are contemplated, but preferably one or two, more preferably one additional agent is used.

"Patient" includes both human and animals. A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

"PG" means protecting group.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzothiadiazolyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cycloheptyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like, "Benzofused cycloalkyl", "benzofused cycloalkenyl", "benzofused heterocycloalkyl", and "benzofused heterocycloalkenyl" mean cycloallyl, cycloalkenyl, heteroycloalkyl or heteroycloalkenyl rings fused to a benzene ring at two adjacent carbon atoms of the non-aromatic rings, for example:

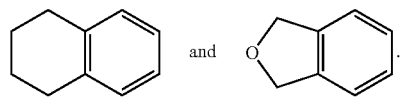 [SMILES: c1ccc2c(c1)CCCC2 ; c1ccc2c(c1)COC2]

The rings are joined to the rest of the molecule by a bond to the non-aromatic ring.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are —(CH$_2$)$_3$—, —(CH$_2$)$_4$—, —O—CH$_2$—O—, —O(CH$_2$)$_2$—O, —O(CH$_2$)$_3$—O, —NH—S—NH—, —NH—O—NH—, or —NH—NH—C(O)—, and the like which form moieties such as, for example:

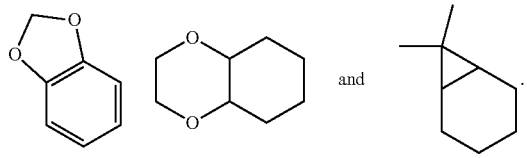

When R$^1$, R$^2$ and/or R$^3$ is an aryl or heteroaryl ring, the ring system substituent can also be a sugar, a polyol, a glucuronide or a sugar carbamate, "Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 or 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" or "heterocycloalkyl" may also be substituted by a moiety which simultaneously replaces two available hydrogens on the same carbon atom on a ring system (e.g., carbonyl). An example of such moiety is:

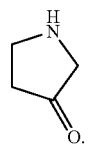

"Heterocyclylalkyl" or "heterocycloalkylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" or "heterocycloalkenyl" means a non-aromatic monocyclic or multicyclic ring system comprising 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also be substituted by a moiety which simultaneously replaces two available hydrogens on the same carbon atom on a ring system (e.g., carbonyl). An example of such moiety is:

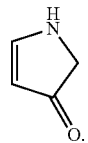

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

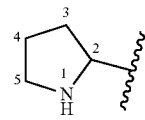

there is no —OH attached directly to carbons marked 2 and 5.

It should also be noted that tautomeric forms such as, for example, the moieties:

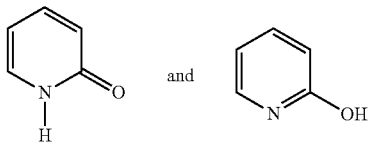 [SMILES: O=c1cccc[nH]1 ; Oc1ccccn1]

are considered equivalent in certain embodiments of this invention.

"Heteroaralkyl" or "heteroarylalkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "rodrug" means a compound (e.g, a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)-aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, $(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula I contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et. al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt (s)" as used herein. Pharmaceutically acceptable (i.e., non-toxic, physiologically acceptable) salts are preferred, although other salts are also useful. Salts of the compounds of the Formula may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-Val; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I, and salts, solvates esters and prodrugs thereof, may exist in their tautomeric form (for example, as an amide or imino ether). All such tautomeric forms are contemplated herein as part of the present invention.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I incorporates a double bond or a fused ring, both the cis- and trans-forms, as well as mixtures, are embraced within the scope of the invention. Also, for example, all keto-enol and imine-enamine forms of the compounds are included in the invention.). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

Certain isotopically-labelled compounds of Formula I (e.g., those labeled with $^{3}H$ and $^{14}C$) are useful in compound and/or substrate tissue distribution assays. Tritiated (i.e., $^{3}H$) and carbon-14 (i.e., isotopes are particularly preferred for their ease of preparation and detectability. Certain isotopically-labelled compounds of Formula I can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula I, in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates, esters and prodrugs of the compounds of Formula I, are intended to be included in the present invention.

Those skilled in the art will appreciate that for some of the compounds of Formula I, one isomer will show greater pharmacological activity than other isomers.

One to three compounds of formula I can be administered in the methods of the invention, preferably one.

Preferably the compound of formula I is administered orally.

The compounds listed above can be administered to an animal orally, intravenously, by inhalation (e.g., to treat fungal infections in the lungs) or topically (e.g. to treat microbial infections of the skin or mucous membranes). Preferably the compound(s) of the invention listed above is administered orally or intravenously, more preferably orally.

For preparing pharmaceutical compositions from the compounds useful in the method of this invention, inert, pharmaceutically acceptable carriers can be either solid or liquid. Solid form preparations include powders, tablets, dispersible granules, capsules, cachets and suppositories. The powders and tablets may be comprised of from about 0.1 to about 99 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds useful in the method of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose.

The quantity of compound listed above in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compound listed above useful in the method of the invention will be regulated according to the judgment of the attending clinician considering such factors as age, condition and size of the patient as well as severity of the symptoms being treated. A typical recommended dosage regimen for a compound listed above is oral administration of about 10 mg to 2000 mg/day preferably 10 to 1000 mg/day, in two to four divided doses to provide relief from the diseases or conditions listed above.

The doses and dosage regimen of the other agents used in the treatment of diseases or conditions listed above will be determined by the attending clinician in view of the approved doses and dosage regimen in the package insert, taking into consideration the age, sex and condition of the patient and the severity of the disease. When administered in combination, the compound(s) of Table 1 and the other agent(s) for treating diseases or conditions listed above can be administered simultaneously or sequentially. This is particularly useful when the components of the combination are preferably given on different dosing schedules, e.g., one component is administered once daily and another every six hours, or when the preferred pharmaceutical compositions are different, e.g. one is preferably a tablet and one is a capsule. A kit comprising the separate dosage forms is therefore advantageous.

When the invention comprises a combination of one or more compounds listed above and one or more other antifungal agents, the active components may be co-administered simultaneously or sequentially, or a single pharmaceutical composition comprising one or more compounds listed above and one or more other antifungal agents in a pharmaceutically acceptable carrier can be administered. The components of the combination can be administered individually or together in any conventional dosage form such as capsule, tablet, powder, cachet, suspension, solution, suppository, nasal spray, etc. The dosages of the other antifungal agents can be determined from published material, and may range from 1 to 1000 mg per dose. When used in combination, the dosage levels of the individual components are preferably lower than the recommended individual dosages because of the advantageous effect of the combination.

When separate pharmaceutical compositions of compounds listed above and other antifungal agents are to be administered, they can be provided in a kit comprising in a single package, one container comprising one or more compounds of the present invention listed above in a pharmaceutically acceptable carrier, and a separate container comprising one or more other antifungal agents in a pharmaceutically acceptable carrier, with the compounds listed above and the other antifungal agents being present in amounts such that the combination is therapeutically effective. A kit is advantageous for administering a combination when, for example, the components must be administered at different time intervals or when they are in different dosage forms.

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

General Methods

The general methods described in this paragraph were used unless stated otherwise in the examples below. All solvents and reagents were used as received. Proton NMR spectra were obtained using a Varian XL-400 (400 MHz) instrument and were reported as parts per million (ppm) downfield from $Me_4Si$. LCMS analysis was performed using an Applied Biosystems API-100 mass spectrometer equipped with a Shimadzu SCL-10A LC column: Altech platinum C18, 3 um, 33 mm×7 mm ID; gradient flow: 0 min, 10% $CH_3CN$; 5 min, 95% CH$_3$CN; 7 min, 95% CH$_3$CN; 7.5 min, 10% CH$_3$CN; 9 min, stop. Flash column chromatography was performed using Selecto Scientific flash silica gel, 32-63 mesh. Analytical and preparative TLC was performed using Analtech Silica gel GF plates. Chiral HPLC was performed using a Varian PrepStar system equipped with a Chiralpak OD column (Chiral Technologies).

In the Schemes and examples that follow, the following abbreviations are used: DMED (dimethylethylenediamine); Ac (acetyl); Me (methyl); Et (ethyl); Ph (phenyl); Bn (benzyl); Boc (tert-butoxycarbonyl); DCE (dichloroethane); DMSO (d$_6$-dimethylsulfoxide); DIPEA (diisopropylethylamine); Dioxane (1,4-dioxane); EtOAc (ethyl acetate); EtOH (ethanol); Ether (diethyl ether); HOBT (1-hydroxybenzotriazole hydrate); IPA (isopropyl alcohol); LCMS (liquid chromatography mass spectrometry); LDA (lithium diisopropylamide); LHMSD (lithium bis(trimethylsilyl)amide); MeOH (methanol); RT (Room temperature, about 25 □C); SiO$_2$ gel for flash chromatography); TFA (trifluoroacetic acid); TLC (thin layer chromatography); THF (tetrahydrofuran).

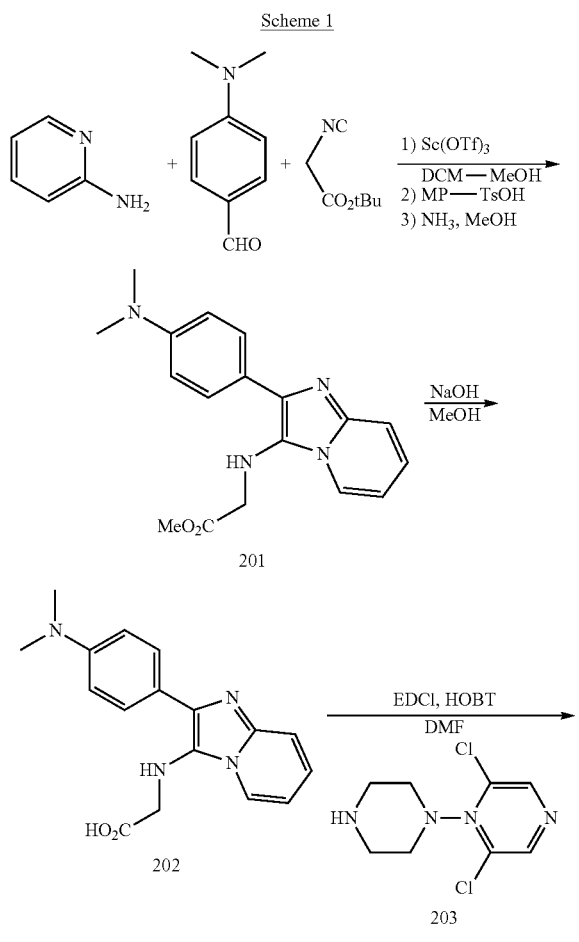

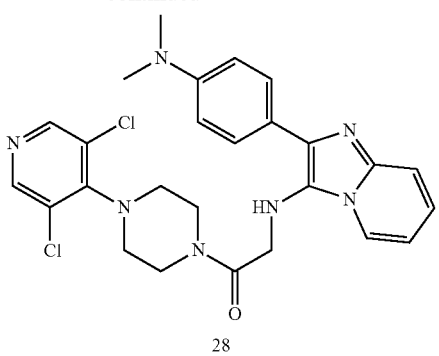

To a DCM-MeOH (3:1) solution (21 mL) of aminopyrazine (1.00 g, 10.62 mmol), 4-(dimethylamino)benzaldehyde (1.90 g, 12.74 mmol, and scandium(III) trifluoromethanesulfonate (261 mg, 0.53 mmol) at room temperature was added tert-butylisocyanoacetate (1.90 mL, 13.1 mmol). The reaction mixture was stirred at room temperature for 36 hrs. The solution was treated with MP-TsOH resin (4.13 mmol/g, 12.9 g, 53.3 mmol) and stirred at room temperature for 18 hr. The resin was filtered, washed with DCM (3×), MeOH (3×) and dried in vacuo. The resin was treated with 2N NH$_3$-MeOH (50 mL) for 1 hour. The solvent was filtered off and the resin washed with both DCM and MeOH. The combined filtrate was concentrated in vacuo and dried in vacuo to afford the desired methyl ester 201 (2.88 g, 9.65 mmol).

The methyl ester 201 (2.65 g, 8.88 mmol) was dissolved in MeOH (75 mL) and 1N sodium hydroxide solution (9.8 mL, 9.8 mmol) was added. The reaction mixture was stirred at room temperature overnight. The solvent was concentrated in vacuo to afford the desired acid 202 (3.04 g, 9.17 mmol).

To a DMF (2 mL) solution of the acid 202 (46.4 mg, 0.14 mmol), amine 203 (39.0 mg, 0.168 mmol) and HOBT (23 mg, 0.170 mmol), at room temperature under nitrogen, was added EDCI (35 mg, 0.183 mmol). The reaction mixture was stirred at room temperature for 18 hours. Ethyl acetate and 1N NaOH were added. The two layers were separated. The aqueous layer was back extracted with ethyl acetate (2×). The organic layers were combined, washed with water (3×), dried over Na$_2$SO$_4$ and concentrated in vacuo. The crude product was purified by flash chromatography [0-8%, (2N NH$_3$-MeOH)-DCM] to afford the desired amide 28 (687 mg).

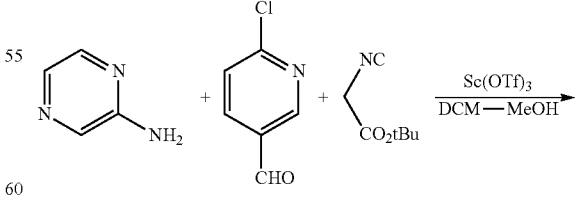

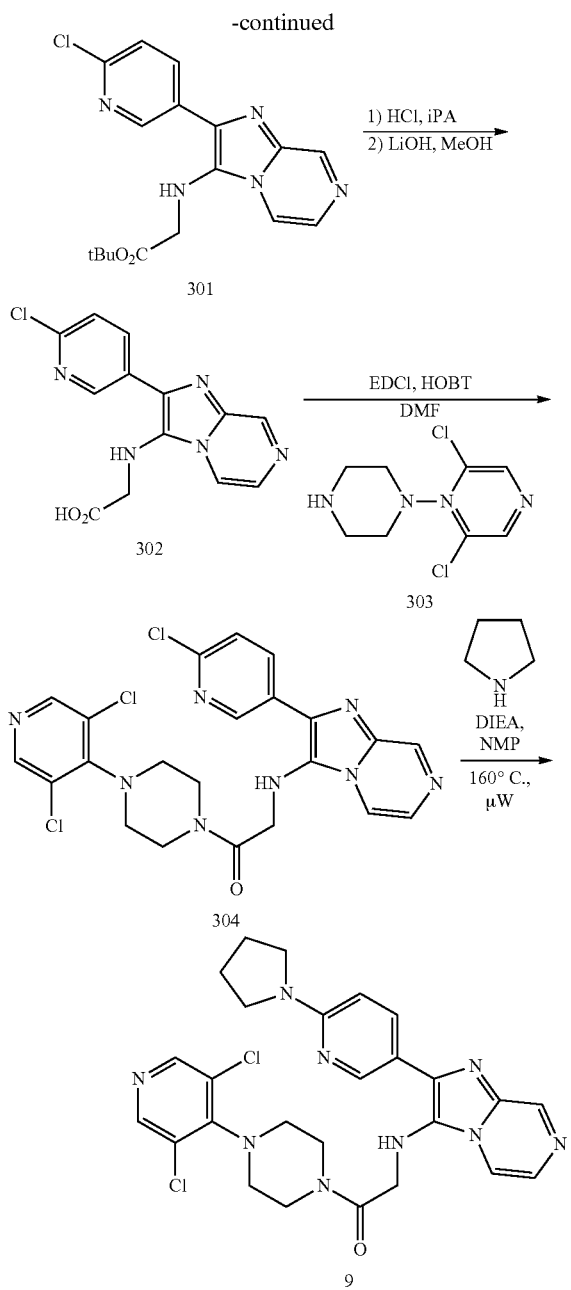

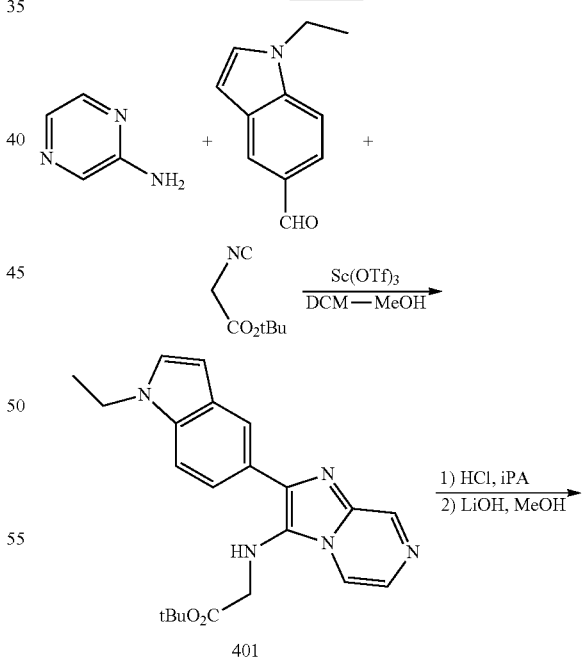

lithium hydroxide (143 mg, 3.40 mmol). The reaction mixture was heated in a microwave reactor at 100° C. for 10 minutes. The solvent was evaporated in vacuo to afford the desired acid 302 (1.06 g, 3.41 mmol).

To a DMF (2 mL) solution of acid 302 (500 mg, 1.61 mmol), amine 303 (375 mg, 1.62 mmol) and HOST (262 mg, 1.94 mmol), at room temperature under nitrogen, was added EDCI (403 mg, 2.10 mmol). The reaction mixture was stirred at room temperature for 18 hours. Ethyl acetate and 1N NaOH were added. The two layers were separated. The aqueous layer was back extracted with ethyl acetate (2×). The organic layers were combined, washed with water (3×), dried over $Na_2SO_4$ and concentrated in vacuo. The crude product was purified by flash chromatography [0-10%, (2N NH3-MeOH)-DCM] to afforded the desired amide 304 (41.3 mg, 0.079 mmol).

A NMP (0.5 mL) solution of the chloropyridine 304 (41.1 mg, 0.079 mmol), pyrrolidine (66 uL, 0.791 mmol) and diisopropylethylamine (55 uL, 0.32 mmol) was heated at 160° C. in a microwave reactor for 1 hour. Additional pyrrolidine (33 µL, 0.40 mmol) was added and the solution was heated in a microwave reactor at 160° C. for an additional 1 hour. Acetic acid (0.10 mL) was added and the crude product was purified by reverse-phase HPLC ($H_2O$:MeCN=95:5 to 5:95 WI 0.1% formic acid). The solvent was concentrated in vacuo. The residue was dissolved in DCM and washed with 1N NaOH. The aqueous layer was back extracted with DCM (2×). The organic layers were combined, dried over $Na_2SO_4$ and concentrated in vacuo to afford the desired product 9 (32 mg).

To a DCM-MeOH (3:1) solution (21 mL) of aminopyrazine (1.0 g, 10.51 mmol), 6-chloropyridine-3-carboxaldehyde (1.78 g, 12.31 mmol) and scandium(III) trifluoromethanesulfonate (259 mg, 0.53 mmol) at room temperature was added tert-butylisocyanoacetate (1.85 mL, 12.72 mmol). The reaction mixture was stirred at room temperature for 3 hours. Additional tert-butylisocyanoacetate (0.4 mL, 2.75 mmol) was added and let stir at room temperature for 18 hours. The solvent was removed in vacuo and the crude product was purified by flash chromatography [0-6%, (2N $NH_3$-MeOH)-DCM] to afford the desired t-butyl ester 301 (1.96 g, 5.49 mmol).

The t-butyl ester 301 (1.96 g, 5.49 mmol) in isopropanol (60 mL) was treated with HCl in isopropanol (30 mL) at 70° C. for 6 hours. The solvent was evaporated in vacuo to afford the corresponding isopropyl ester (2.10 g). To the isopropyl ester (1.06 g, 3.07 mmol) was added methanol (15 mL) and

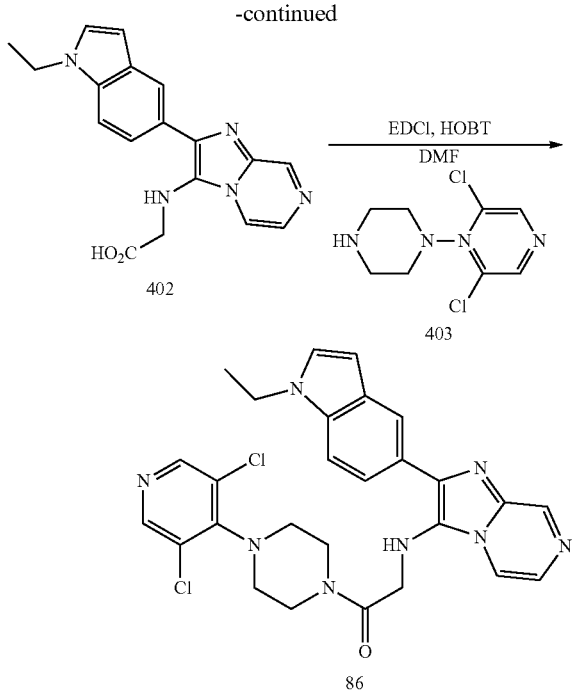

To a DCM-MeOH (3:1) solution (5 mL) of aminopyrazine (246 mg, 2.59 mmol), ethyl-2,3-dihydro-1H-indole-5-carboxaldehyde (498.4 mg, 2.84 mmol) and scandium(III) trifluoromethanesulfonate (65 mg, 0.13 mmol) at room temperature was added tert-butylisocyanoacetate (0.45 mL, 3.09 mmol). The reaction mixture was stirred at room temperature for 18 hr. The solvent was evaporated in vacuo and the crude product was purified by flash chromatography (EtOAc-Hex=1:4 to 8:1) to afford the desired t-butyl ester 401 (802.2 mg, 2.04 mmol).

The t-butyl ester 401 (768.2 mg, 1.95 mmol) in isopropanol (6 mL) was treated with HCl in isopropanol (3 mL) at 70° C. for 18 hours. The solvent was evaporated in vacuo. The residue was dissolved in DCM and washed with 1N NaOH. The aqueous layer was back extracted with DCM (2×). The organic layers were combined, dried over Na$_2$SO$_4$ and concentrated in vacuo to afford the corresponding isopropyl ester (528.5 mg). To the isopropyl ester (423 mg, 1.11 mmol) was added MeOH (5 mL) and lithium hydroxide (52 mg, 1.24 mmol). The reaction mixture was heated in a microwave reactor at 100° C. for 10 minutes. The solvent was evaporated in vacuo to afford the desired acid 402 (421.4 mg, 1.23 mmol).

To a DMF (1.5 mL) solution of the acid 402 (35 mg, 0.102 mmol), amine 403 (27 mg, 0.116 mmol) and HOBT (16.6 mg, 0.123 mmol), at room temperature under nitrogen, was added EDCI (26.0 mg, 0.136 mmol). The reaction mixture was stirred at room temperature for 18 hours. Ethyl acetate and 1N NaOH were added. The two layers were separated. The aqueous layer was back extracted with ethyl acetate (2×). The organic layers were combined, washed with water (3×), dried over Na$_2$SO$_4$ and concentrated in vacuo. The crude product was purified by flash chromatography to afford the desired amide 86 (32.1 mg) as a viscous yellow liquid.

Using procedures analogous to those described above, the compounds of table 1 were synthesized.

TABLE 1

| ID | Structure | M + H |
|----|-----------|-------|
| 1  | 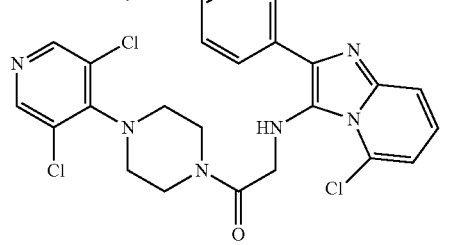 | 601.3 |
| 2  | 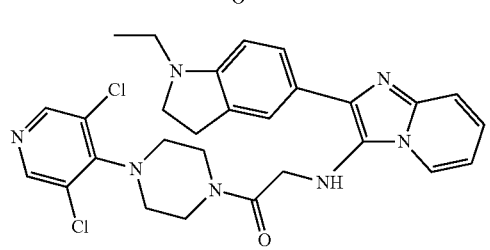 | 550.3 |
| 3  | 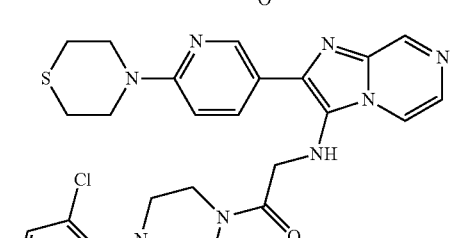 | 584.3 |
| 4  | 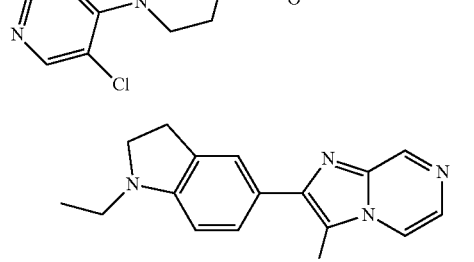 | 551.3 |
| 5  | 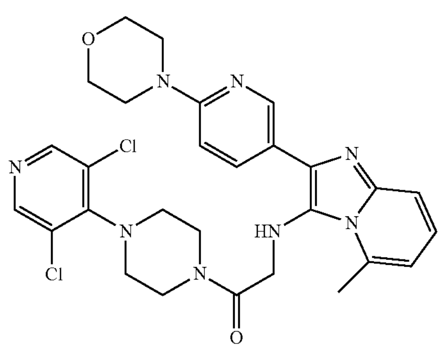 [SMILES: Cc1cccc2nc(-c3ccc(N4CCOCC4)nc3)c(NCC(=O)N3CCN(c4c(Cl)cncc4Cl)CC3)n12] | 581.3 |

TABLE 1-continued

| ID | Structure | M+H |
|---|---|---|
| 6 | 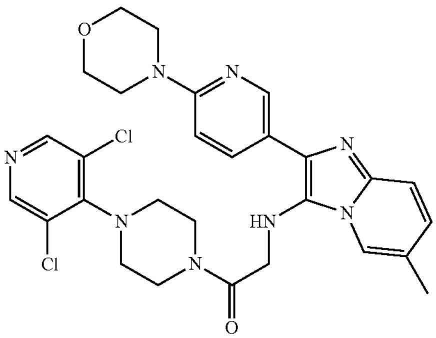 [SMILES: Cc1ccc2nc(-c3ccc(N4CCOCC4)nc3)c(NCC(=O)N3CCN(c4c(Cl)cncc4Cl)CC3)n2c1] | 581.3 |
| 7 | 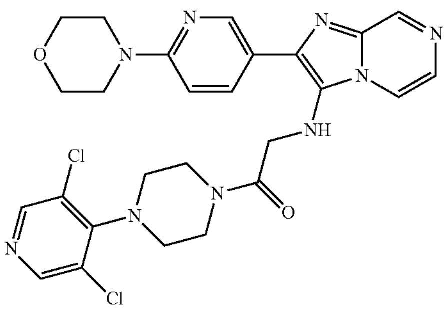 [SMILES: O=C(CNc1c(-c2ccc(N3CCOCC3)nc2)nc2cnccn12)N1CCN(c2c(Cl)cncc2Cl)CC1] | 568.3 |
| 8 | 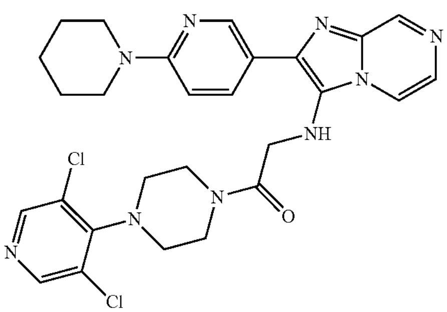 [SMILES: O=C(CNc1c(-c2ccc(N3CCCCC3)nc2)nc2cnccn12)N1CCN(c2c(Cl)cncc2Cl)CC1] | 566.3 |
| 10 | 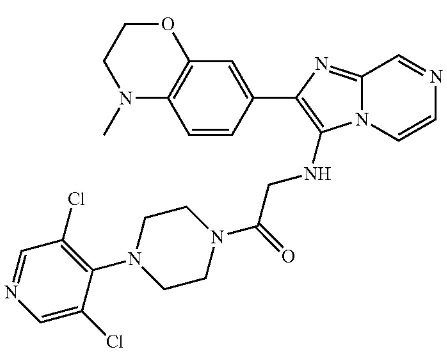 [SMILES: CN1CCOc2cc(-c3nc4cnccn4c3NCC(=O)N3CCN(c4c(Cl)cncc4Cl)CC3)ccc21] | 553.3 |
| 11 | | 565.3 |
| 12 | | 526.3 |
| 13 | | 551.3 |
| 14 | | 579.3 |

TABLE 1-continued

| ID | Structure | M + H |
|---|---|---|
| 15 | | 565.3 |
| 16 | | 516.3 |
| 17 | | 565.3 |
| 18 | | 515.3 |
| 19 | 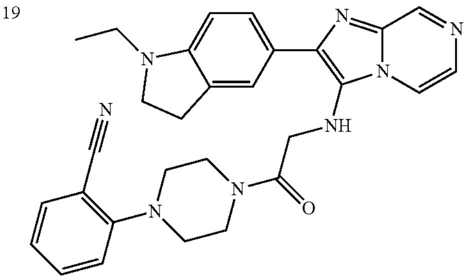 | 507.3 |
| 20 | 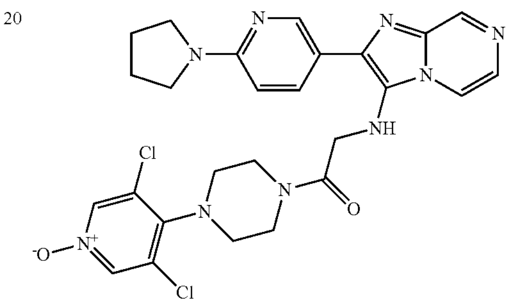 | 568.3 |
| 21 | 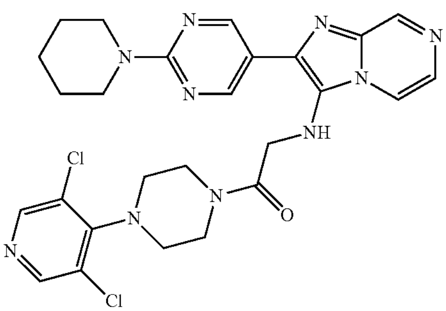 [SMILES: O=C(CNc1c(-c2cnc(N3CCCCC3)nc2)nc2cnccn12)N1CCN(c2c(Cl)cncc2Cl)CC1] | 567.3 |
| 22 | 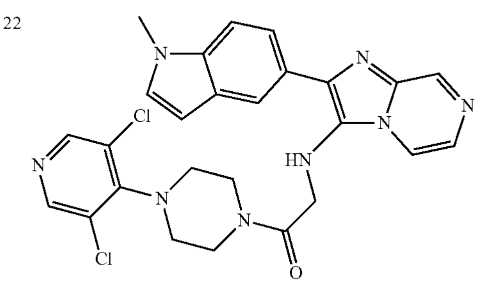 | 535.3 |
| 23 | 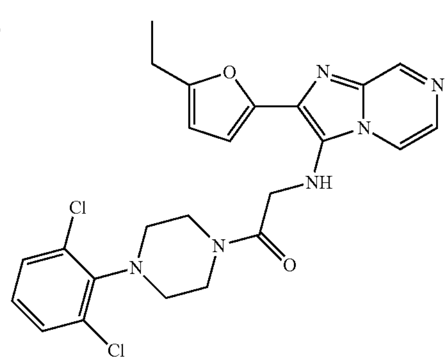 [SMILES: CCc1ccc(-c2nc3cnccn3c2NCC(=O)N2CCN(c3c(Cl)cccc3Cl)CC2)o1] | 499.3 |

TABLE 1-continued

| ID | Structure | M+H |
|----|-----------|-----|
| 24 | 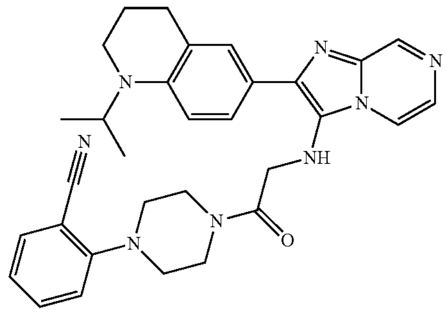 [SMILES: CC(C)N1CCCc2cc(-c3nc4cnccn4c3NCC(=O)N3CCN(c4ccccc4C#N)CC3)ccc21] | 535.3 |
| 25 | 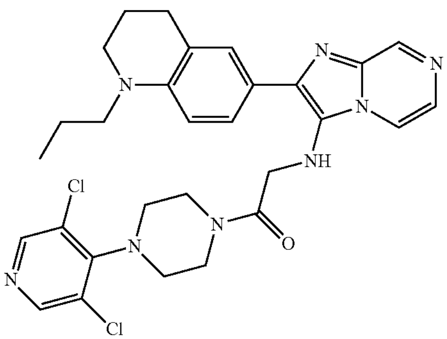 [SMILES: CCCN1CCCc2cc(-c3nc4cnccn4c3NCC(=O)N3CCN(c4c(Cl)cncc4Cl)CC3)ccc21] | 579.3 |
| 26 | 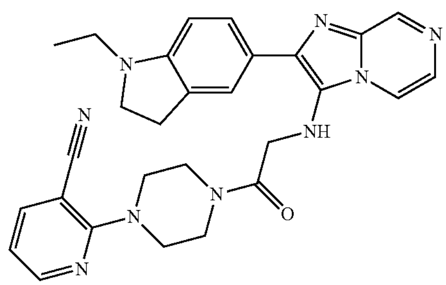 [SMILES: CCN1CCc2cc(-c3nc4cnccn4c3NCC(=O)N3CCN(c4ncccc4C#N)CC3)ccc21] | 508.3 |
| 27 | 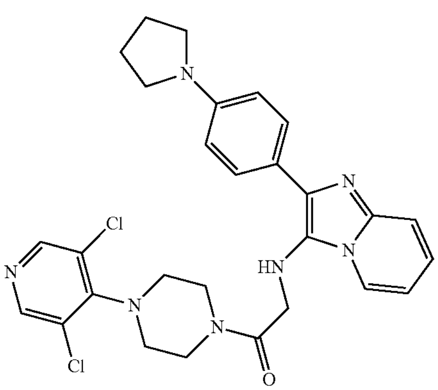 [SMILES: O=C(CNc1c(-c2ccc(N3CCCC3)cc2)nc2ccccn12)N1CCN(c2c(Cl)cncc2Cl)CC1] | 550.3 |
| 29 | | 509.3 |
| 30 | | 515.3 |
| 31 | | 489.3 |
| 32 | | 551.3 |

TABLE 1-continued

| ID | Structure | M + H |
|---|---|---|
| 33 | | 551.3 |
| 34 | | 495.3 |
| 35 | | 506.3 |
| 36 | | 507.3 |
| 37 | | 509.3 |
| 38 | 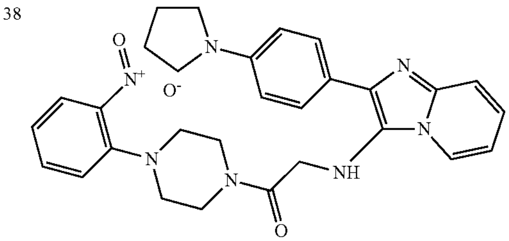 | 526.3 |
| 39 | 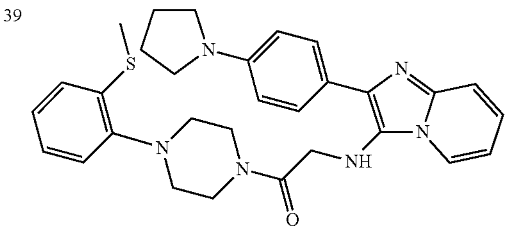 | 527.3 |
| 40 | 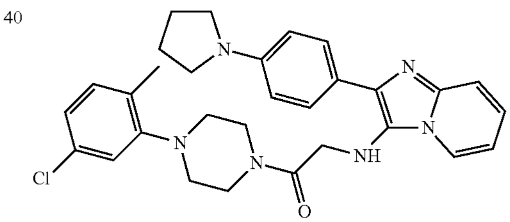 | 529.3 |
| 41 | 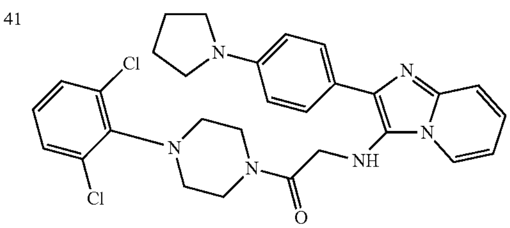 | 549.3 |
| 42 | 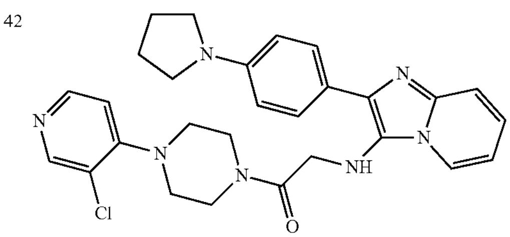 [SMILES: Cc1ccc(Cl)cc1N1CCN(C(=O)CNc2c(-c3ccc(N4CCCC4)cc3)nc3ccccn23)CC1] | 516.3 |
| 43 | 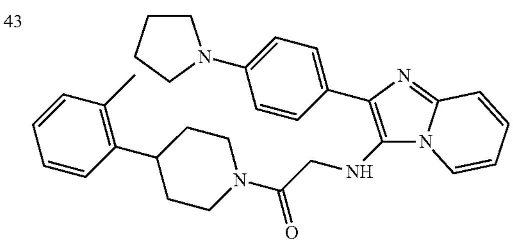 | 494.3 |

TABLE 1-continued

| ID | Structure | M + H |
|---|---|---|
| 44 | 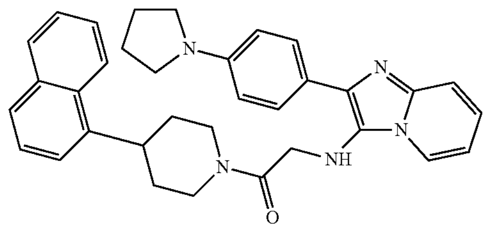 [SMILES: O=C(CNc1c(-c2ccc(N3CCCC3)cc2)nc2ccccn12)N1CCC(c2cccc3ccccc23)CC1] | 530.3 |
| 46 | 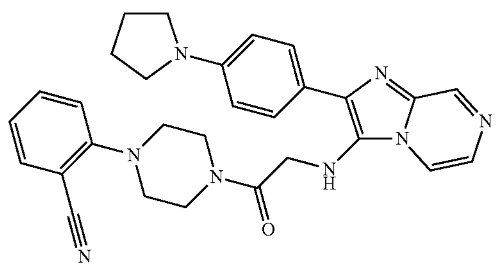 [SMILES: N#Cc1ccccc1N1CCN(C(=O)CNc2c(-c3ccc(N4CCCC4)cc3)nc3cnccn23)CC1] | 507.3 |
| 47 | 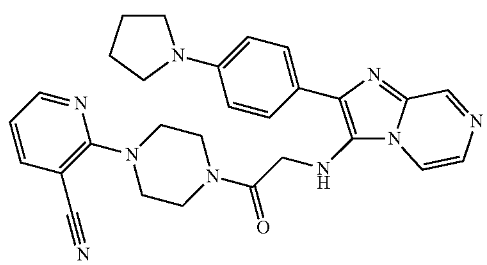 [SMILES: N#Cc1cccnc1N1CCN(C(=O)CNc2c(-c3ccc(N4CCCC4)cc3)nc3cnccn23)CC1] | 508.3 |
| 48 | 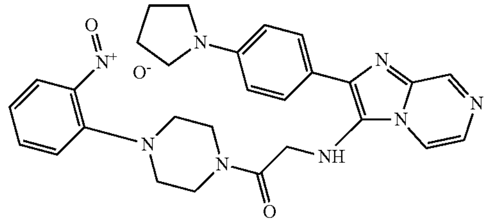 | 527.3 |
| 49 | 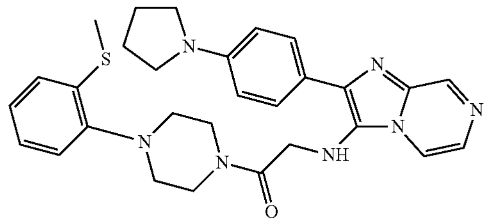 | 528.3 |
| 50 | 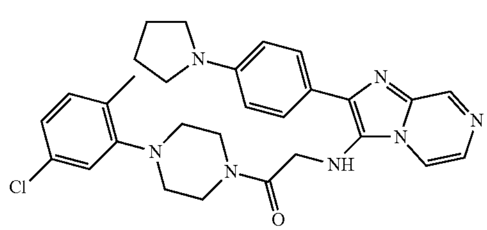 [SMILES: Cc1ccc(Cl)cc1N1CCN(C(=O)CNc2c(-c3ccc(N4CCCC4)cc3)nc3cnccn23)CC1] | 530.3 |
| 51 | | 517.3 |
| 52 | | 531.3 |
| 55 | | 481.3 |
| 56 | | 483.3 |
| 57 | | 523.3 |
| 58 | | 481.3 |

TABLE 1-continued
| ID | Structure | M + H |
|---|---|---|
| 59 | 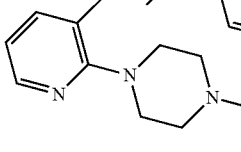 | 482.3 |
| 60 | 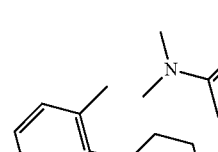 | 504.3 |
| 61 | 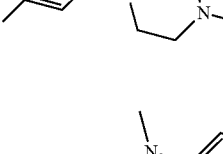 | 524.3 |
| 62 | 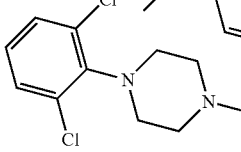 | 505.3 |
| 63 | 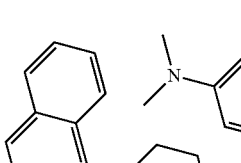 | 535.3 |
| 65 | 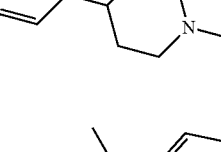 | 523.3 |
| 66 | 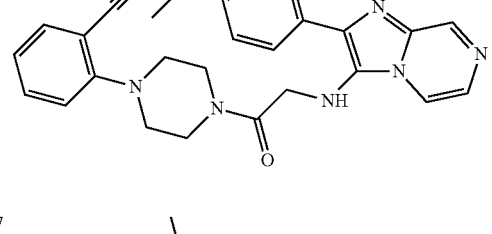 | 480.3 |
| 67 | 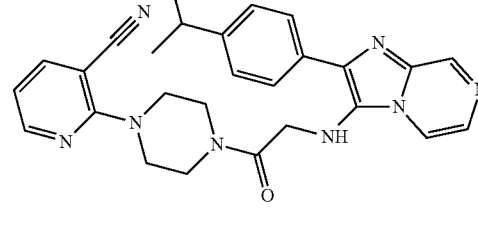 | 481.3 |
| 70 | 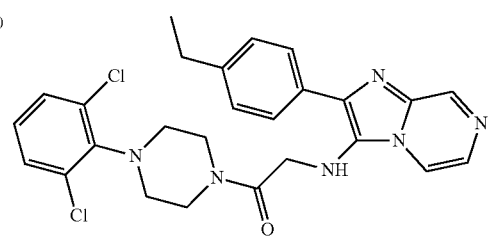 | 509.3 |
| 72 | 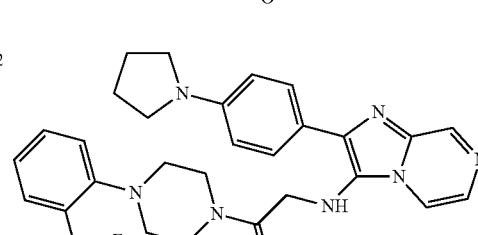 | 550.3 |
| 73 | 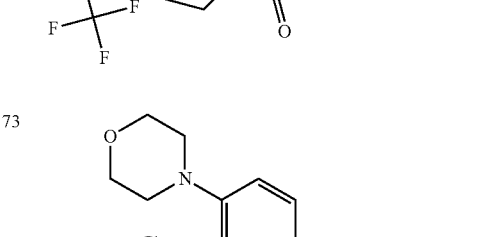 | 566.3 |

TABLE 1-continued
| ID | Structure | M + H |
|---|---|---|
| 74 | 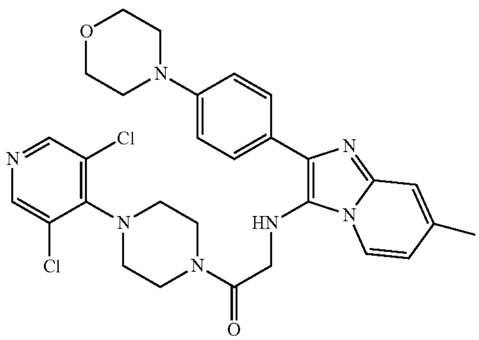 [SMILES: Cc1ccn2c(NCC(=O)N3CCN(c4c(Cl)cncc4Cl)CC3)c(-c3ccc(N4CCOCC4)cc3)nc2c1] | 580.3 |
| 75 | 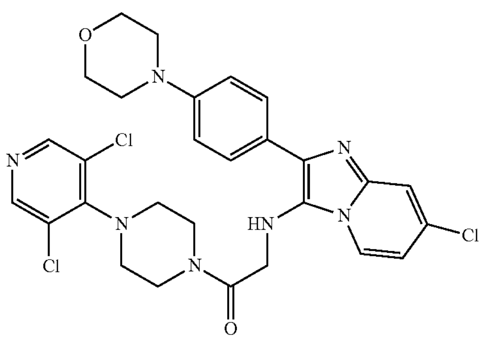 [SMILES: O=C(CNc1c(-c2ccc(N3CCOCC3)cc2)nc2cc(Cl)ccn12)N1CCN(c2c(Cl)cncc2Cl)CC1] | 500.3 |
| 76 | 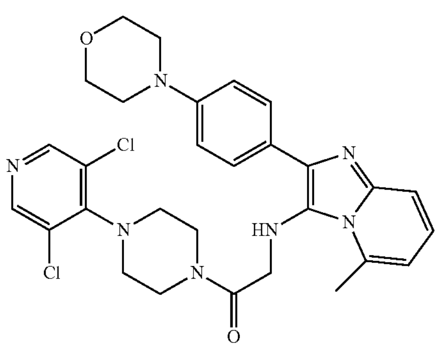 [SMILES: Cc1cccc2nc(-c3ccc(N4CCOCC4)cc3)c(NCC(=O)N3CCN(c4c(Cl)cncc4Cl)CC3)n12] | 580.3 |
| 77 | 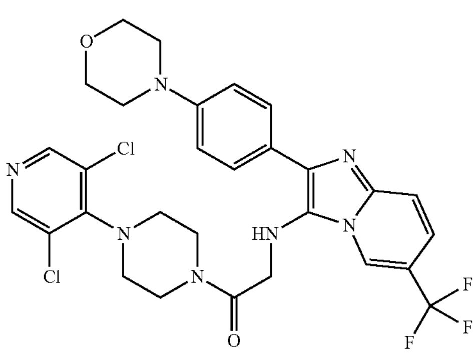 [SMILES: O=C(CNc1c(-c2ccc(N3CCOCC3)cc2)nc2ccc(C(F)(F)F)cn12)N1CCN(c2c(Cl)cncc2Cl)CC1] | 634.4 |
| 78 | 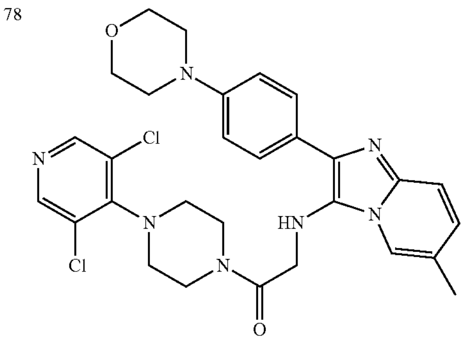 | 580.3 |
| 79 | 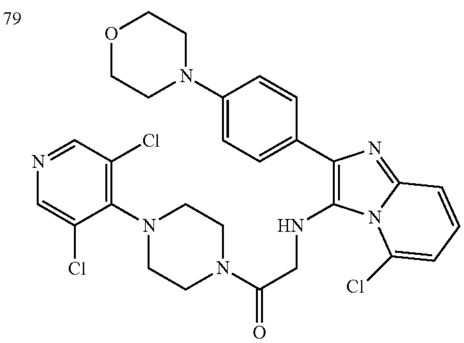 | 600.3 |
| 80 | 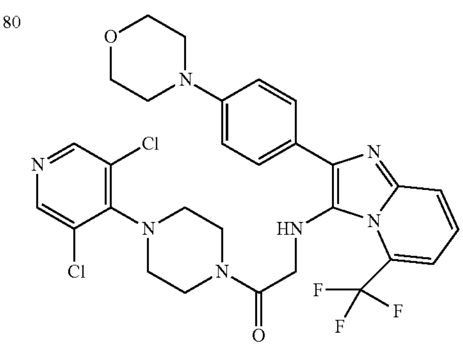 | 634.3 |
| 81 | 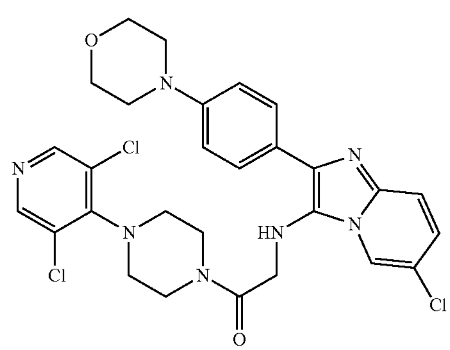 [SMILES: O=C(CNc1c(-c2ccc(N3CCOCC3)cc2)nc2ccc(Cl)cn12)N1CCN(c2c(Cl)cncc2Cl)CC1] | 600.3 |
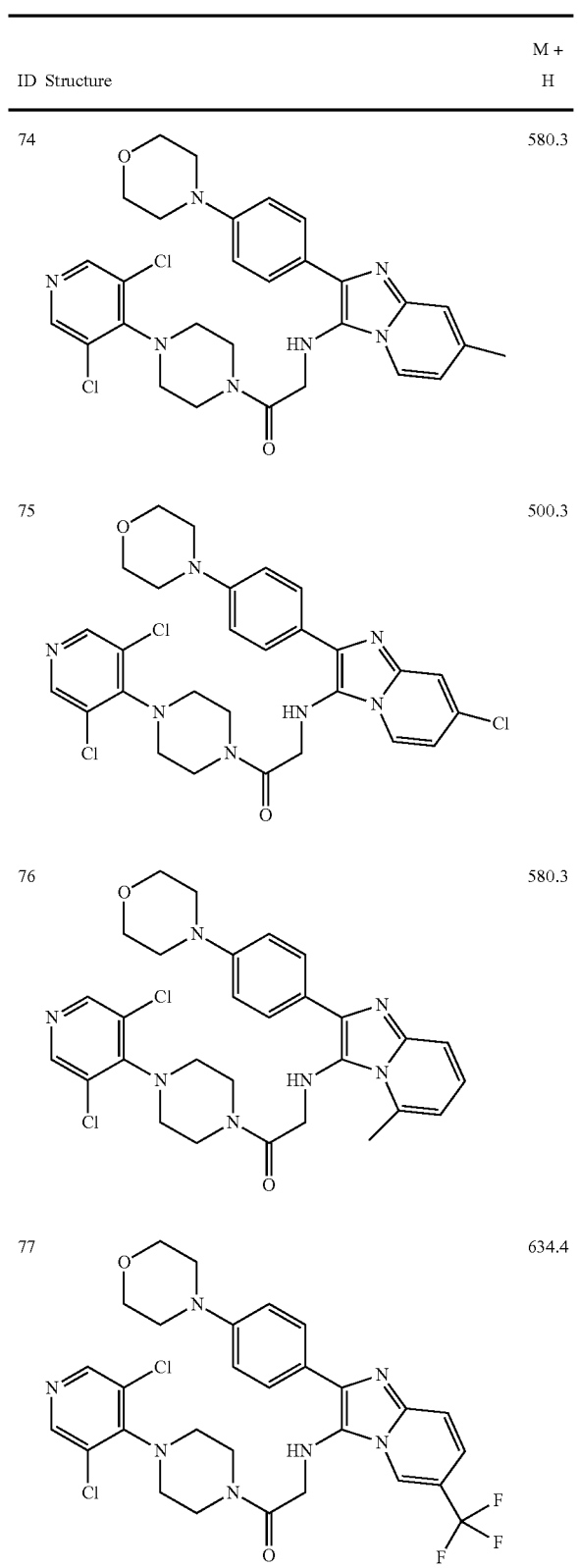
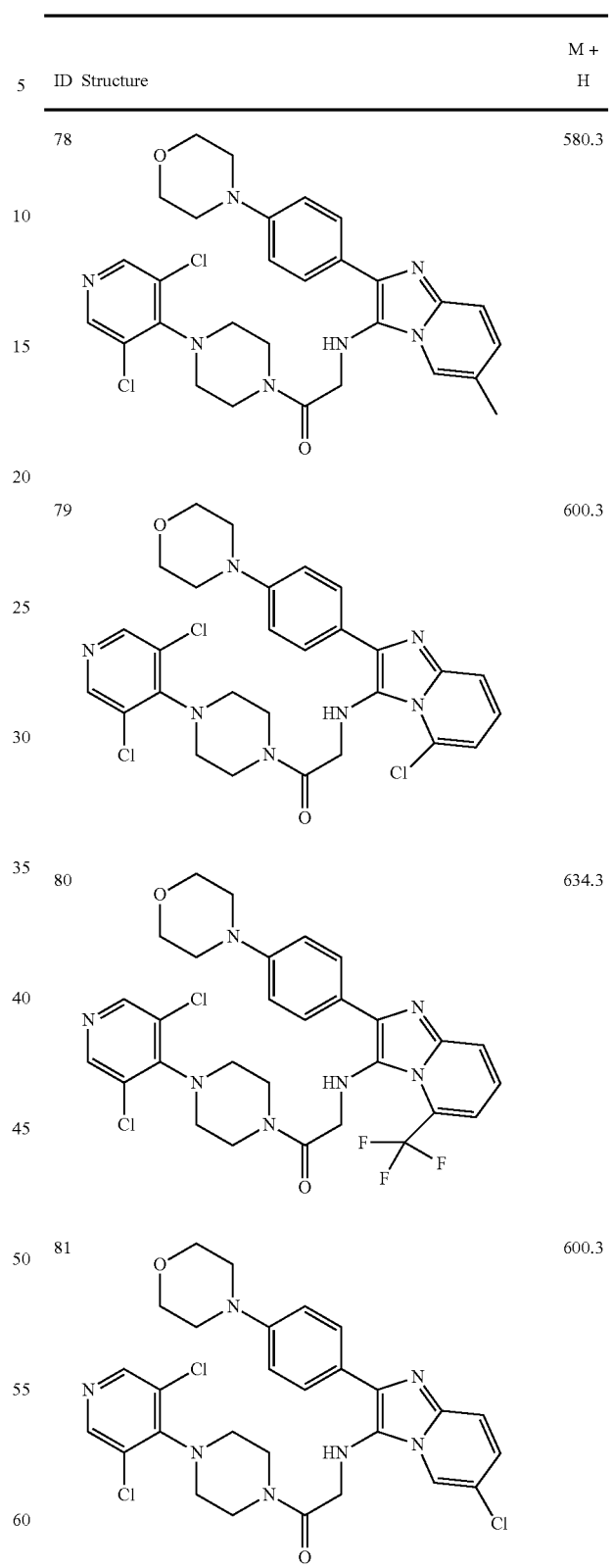

TABLE 1-continued

| ID | Structure | M + H |
|---|---|---|
| 82 | 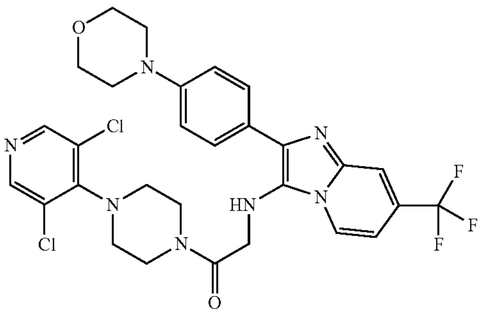 [SMILES: O=C(CNc1c(-c2ccc(N3CCOCC3)cc2)nc2cc(C(F)(F)F)ccn12)N1CCN(c2c(Cl)cncc2Cl)CC1] | 634.3 |
| 83 | 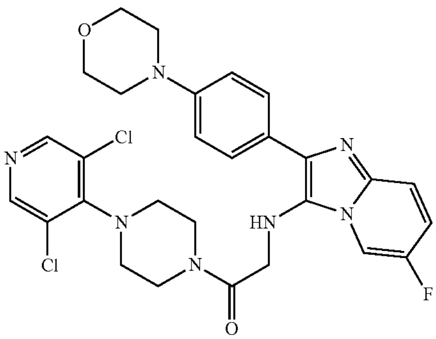 [SMILES: O=C(CNc1c(-c2ccc(N3CCOCC3)cc2)nc2ccc(F)cn12)N1CCN(c2c(Cl)cncc2Cl)CC1] | 584.3 |
| 84 | 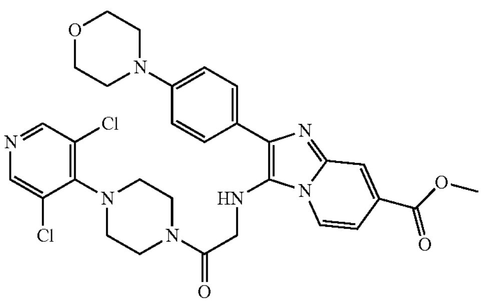 [SMILES: COC(=O)c1ccn2c(NCC(=O)N3CCN(c4c(Cl)cncc4Cl)CC3)c(-c3ccc(N4CCOCC4)cc3)nc2c1] | 624.3 |
| 85 | 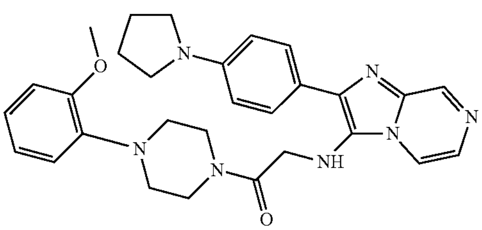 [SMILES: COc1ccccc1N1CCN(C(=O)CNc2c(-c3ccc(N4CCCC4)cc3)nc3cnccn23)CC1] | 509.6 |

Assays

Compounds useful in the method of the invention were investigated for their utility as antimicrobial agents in the following assay.

Susceptibility testing (MIC determinations) was performed using the standard broth microdilution methodology precisely as described in the Clinical Laboratory Standards Institute Document M7-A6; Methods for Dilution Antimicrobial Susceptibility Tests for Bacteria That Grow Aerobically; Approved Standard—Sixth Edition (ISBN 1-56238-486-4), CLSI, 940 West Valley Road, Suite 1400, Wayne, Pa. 19087-1898 USA.

To perform the test, a series of 0.1 ml media in a 96-well plate is prepared with Mueller Hinton broth to which various concentrations of the test compound are added. The media are then inoculated with a standardized suspension of the test organism, *Staphylococcus aureus* ATCC29213. After overnight incubation at 35° C., the tests are examined and the minimal inhibitory concentration (MIC) is determined. MIC is defined as the lowest concentration of an antimicrobial agent that prevents visible growth of a microorganism in the broth microdilution susceptibility test Table 2 contains a list of exemplary compounds which were tested in the above assay. They exhibited MIC values of less than or equal to 8 μg/ml to as low as 0.06 μg/ml.

TABLE 2

| ID | MIC Staph. aureus ATCC-29213 3 μg/ml | ID | MIC Staph. aureus ATCC-29213 3 μg/ml | ID | MIC Staph. aureus ATCC-29213 3 μg/ml | ID | MIC Staph. aureus ATCC-29213 3 μg/ml |
|---|---|---|---|---|---|---|---|
| 1 | 0.06 | 2 | 0.125 | 3 | 0.125 | 4 | 0.19 |
| 5 | 0.25 | 6 | 0.25 | 7 | 0.4 | 8 | 0.44 |
| 9 | 0.46 | 10 | 0.5 | 11 | 0.5 | 12 | 0.5 |
| 13 | 0.96 | 14 | 1 | 15 | 1 | 16 | 2 |
| 17 | 2 | 18 | 3 | 19 | 4 | 20 | 4 |
| 21 | 4 | 22 | 8 | 23 | 8 | 24 | 8 |
| 25 | 8 | 26 | 8 | 27 | 0.06 | 28 | 0.31 |
| 29 | 5 | 30 | 5 | 31 | 5 | 32 | 0.96 |
| 33 | 0.19 | 34 | 5 | 35 | 0.313 | 36 | 0.625 |
| 37 | 0.5 | 38 | 2.5 | 39 | 1 | 40 | 1 |
| 41 | 0.313 | 42 | 2.5 | 43 | 8 | 44 | 4 |
| 46 | 0.313 | 47 | 0.625 | 48 | 4 | 49 | 5 |
| 50 | 2.5 | 51 | 5 | 52 | 5 | 53 | 0.625 |
| 55 | 6 | 56 | 2 | 57 | 0.25 | 58 | 6 |
| 59 | 6 | 60 | 8 | 61 | 0.25 | 62 | 8 |
| 63 | 8 | 65 | 1 | 66 | 8 | 67 | 4 |
| 70 | 4 | 72 | 8 | 73 | 0.09 | 74 | 0.06 |
| 75 | 0.125 | 76 | 0.03 | 77 | 0.06 | 78 | 0.125 |
| 79 | 0.06 | 80 | 0.25 | 81 | 0.25 | 82 | 0.125 |
| 83 | 0.125 | 84 | 0.125 | 85 | 2 | | |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each and every document referred to in this patent application is incorporated herein by reference in its entirety for all purposes.

What is claimed is:

1. The compound of Formula I:

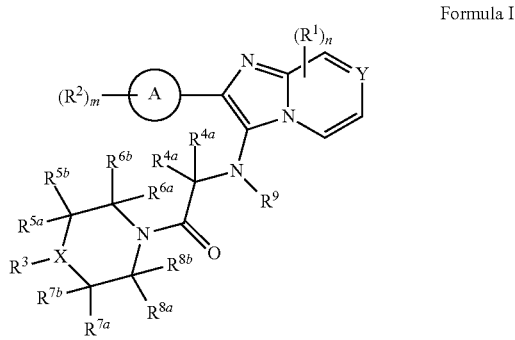

Formula I or a pharmaceutically acceptable salt thereof, wherein:

X is selected from the group consisting of:

(a) CH, and
(b) N;
Y is selected from the group consisting of:
(a) CH, and
(b) N;
ring A is selected from the group consisting of:
(a) cycloalkyl,
(b) cycloalkenyl,
(c) aryl,
(d) heterocyclyl,
(e) heterocyclenyl, and
(f) heteroaryl,
   wherein said cycloalkyl, cycloalkenyl, aryl, heterocyclyl, heterocyclenyl, and heteroaryl is substituted by at least one $R^2$,
   wherein when each of said cycloalkyl, cycloalkenyl, aryl, heterocyclyl, heterocyclenyl, and heteroaryl, has substituents on adjacent carbon atoms, said substituents can optionally be taken together with the carbon atoms to which they are attached to form a five- or six-membered cycloalkyl, cycloalkenyl, heterocyclyl, heterocyclenyl, aryl or heteroaryl, wherein said five- or six-membered cycloalkyl, cycloalkenyl, heterocyclyl, aryl or heteroaryl is unsubstituted or substituted by at least one $R^2$;
each $R^1$ is independently selected from the group consisting of:
(a) halo,
(b) alkyl,
(c) alkoxyl,
(d) —CN,
(e) —NH$_2$,
(f) —N(alkyl)$_2$,
(g) —N(H)alkyl, and
(h) haloalkyl;
each $R^2$ is independently selected from the group consisting of:
(a) alkyl,
(b) alkoxyl,
(c) haloalkyl,
(d) alkenyl,
(e) alkynyl,
(f) —NH$_2$,
(g) —N(alkyl)$_2$,
(h) —N(H)alkyl,
(i) halogen,
(j) —CN,
(k) —OH, and
(l) heterocyclyl;
$R^3$ is selected from the group consisting of:
(a) haloalkyl,
(b) alkoxyl,
(c) —NH$_2$,
(d) —NH(alkyl),
(e) —N(alkyl)$_2$,
(f) aryl,
(g) heteroaryl, and
(h) heteroaryl-N-oxide,
   wherein each of said aryl, heteroaryl, or heteroaryl-N-oxide is independently unsubstituted or substituted with one or more substituents independently selected from the group consisting of alkyl, haloalkyl, alkoxyl, thioalkoxyl, NO$_2$, halo and —CN;
$R^{4a}$ and $R^{4b}$ are independently selected from the group consisting of:
(a) hydrogen,
(b) alkyl, and
(c) haloalkyl;
Rhu 5a, $R^{5b}$, $R^{6a}$, $R^{6b}$, $R^{7a}$, $R^{7b}$, $R^{8a}$ and $R^{8b}$ are independently selected from the group consisting of:
(a) hydrogen,
(b) alkyl, and
(c) haloalkyl;
$R^9$ is selected from the group consisting of:
(a) hydrogen,
(b) alkyl, and
(c) haloalkyl; and
m is 1, 2, 3, or 4,
n is 0, 1, 2, 3 or 4,
with the proviso that when Y is N, and Ring A is aryl, $R^3$ is not

[structures shown]

2. The compound of claim 1, ring A is selected from the group consisting of:
(a) phenyl,
(b) pyridinyl,
(c) pyrimidinyl,
(d) indolinyl,
(e) indolyl,
(f) benzo-morpholinyl,
(g) tetrahydroquinolinyl,
(h) thienyl, and
(i) furanyl,
   wherein said phenyl, pyridinyl, pyrimidinyl, indolinyl, indolyl, benzo-morpholinyl, tetrahydroquinolinyl, thienyl, and furanyl is substituted by at least one $R^2$.

3. The compound of claim 2, wherein $R^3$ is selected from the group consisting of

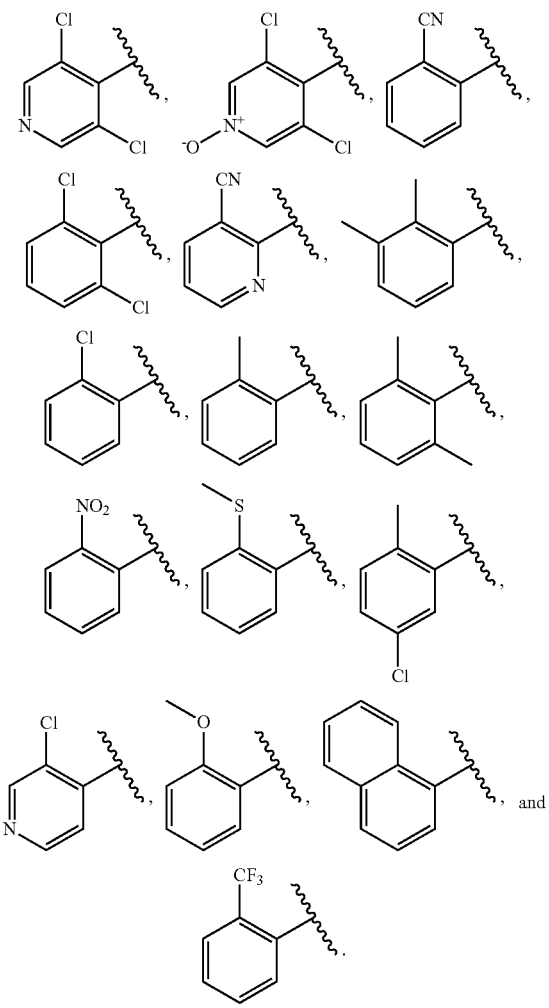

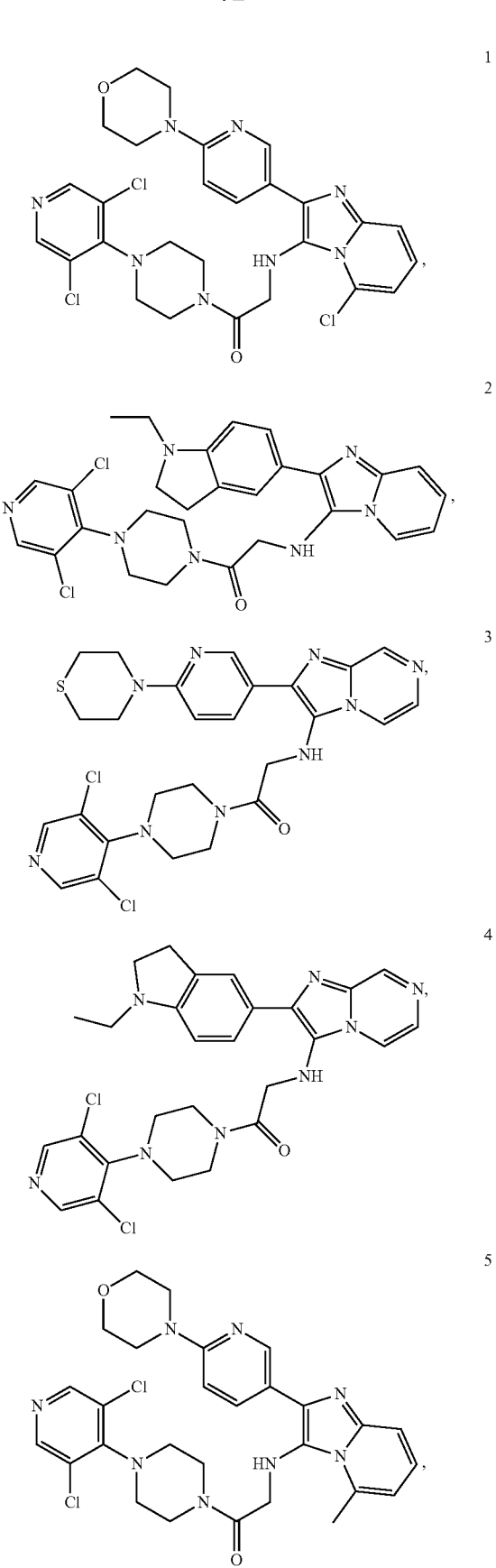

4. The compound of claim 3, X is N;
R$^{4a}$ and R$^{4b}$ are each hydrogen; and
R$^{5a}$, R$^{5b}$, R$^{6a}$, R$^{6b}$, R$^{7a}$, R$^{7b}$, R$^{8a}$ and R$^{8b}$ are each hydrogen.

5. The compound of claim 4, wherein:
each R$^1$ is selected from the group consisting of:
 (a) chloro, and
 (b) methyl; and
each R$^2$ is selected from the group consisting of:
 (a) methyl,
 (b) ethyl,
 (c) propyl,
 (d) isopropyl,
 (e) —N(CH$_3$)$_2$,
 (f) pyrrolidinyl,
 (g) piperidinyl,
 (h) thiomorpholinyl, and
 (i) morpholinyl.

6. The compound of claim 1, selected from the group consisting of:

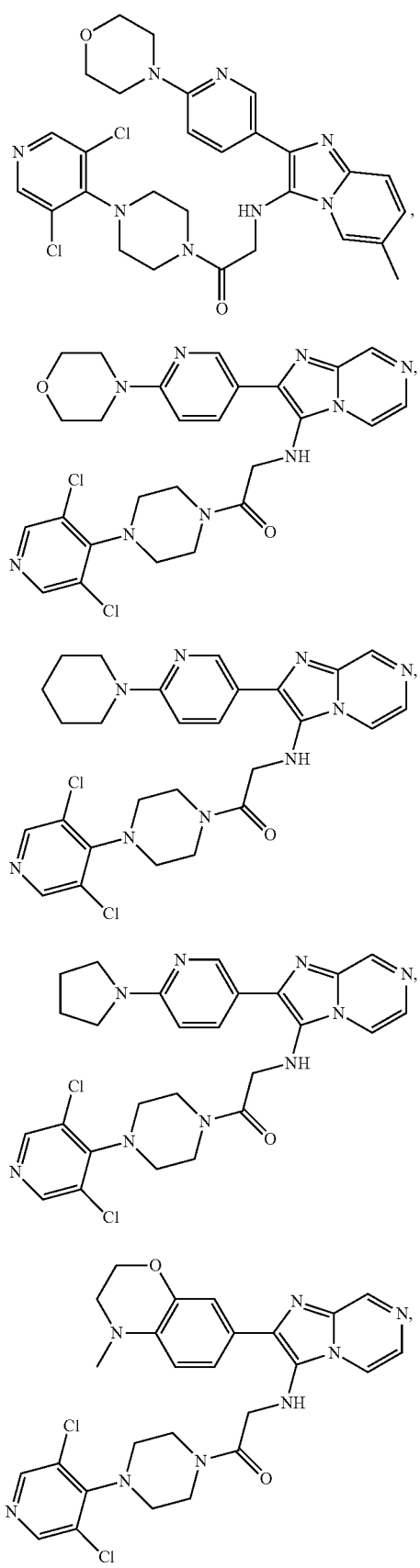
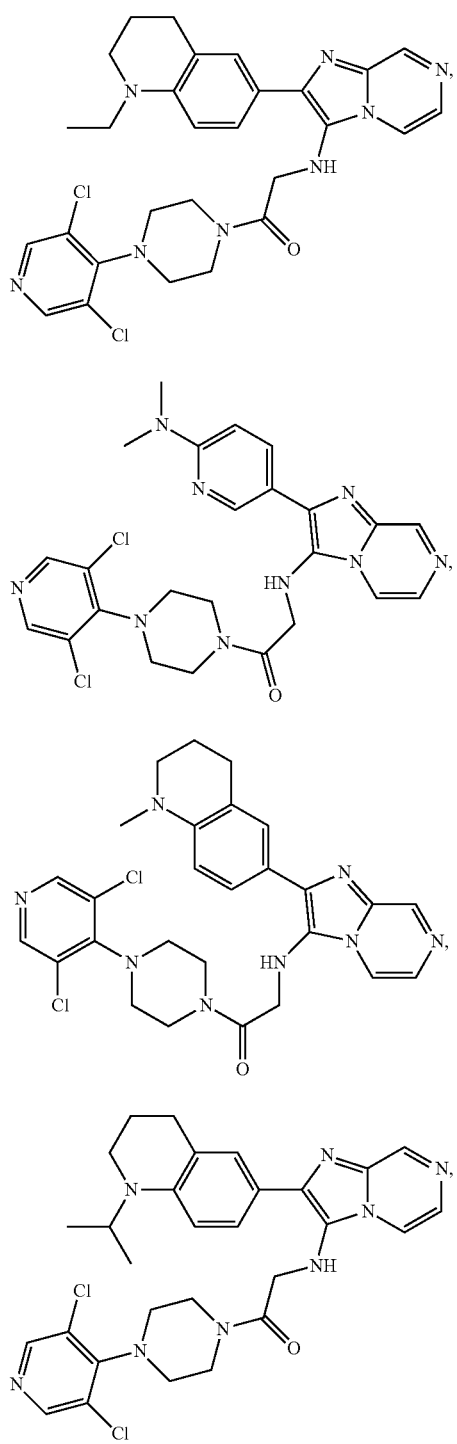

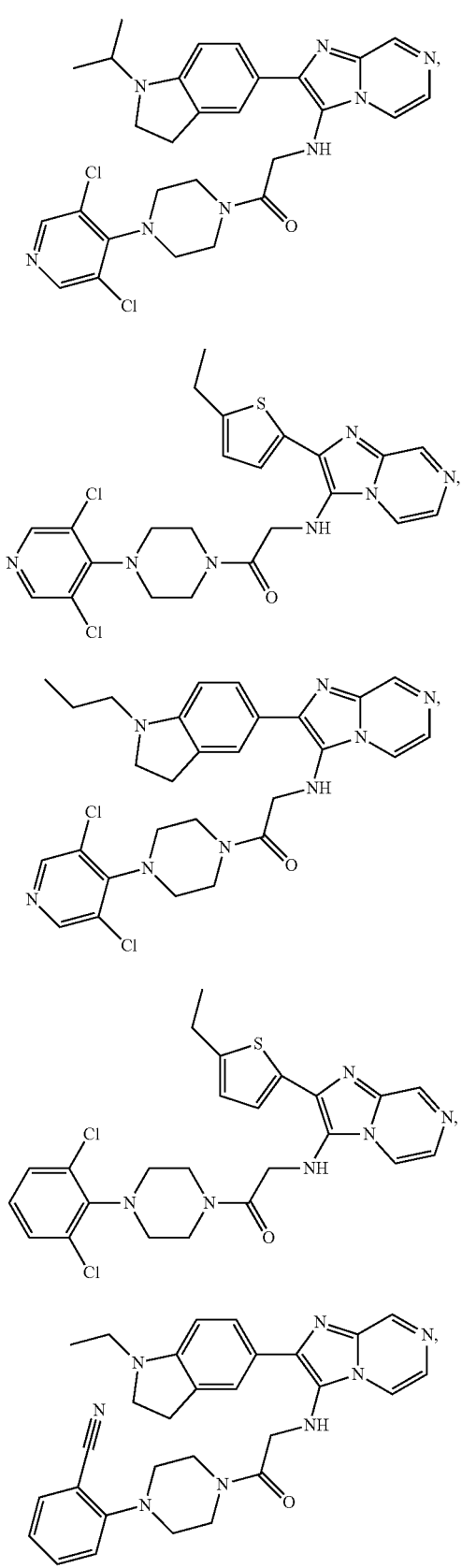
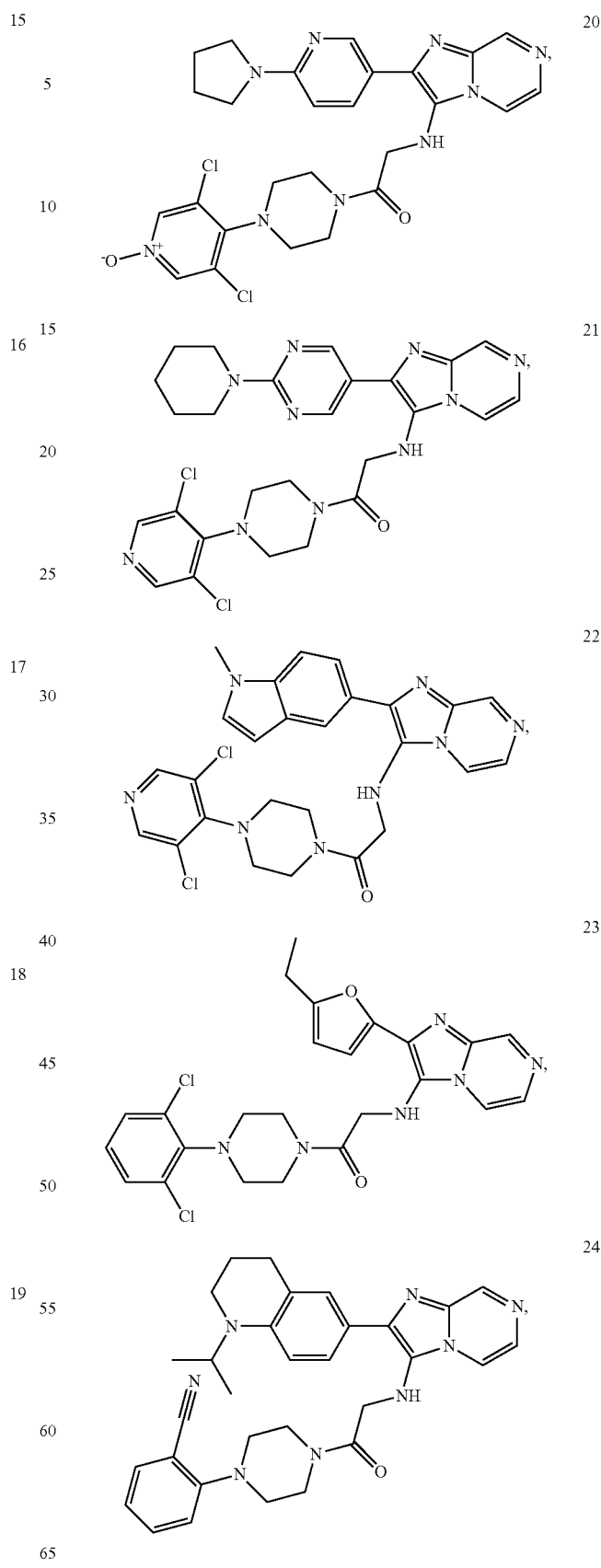

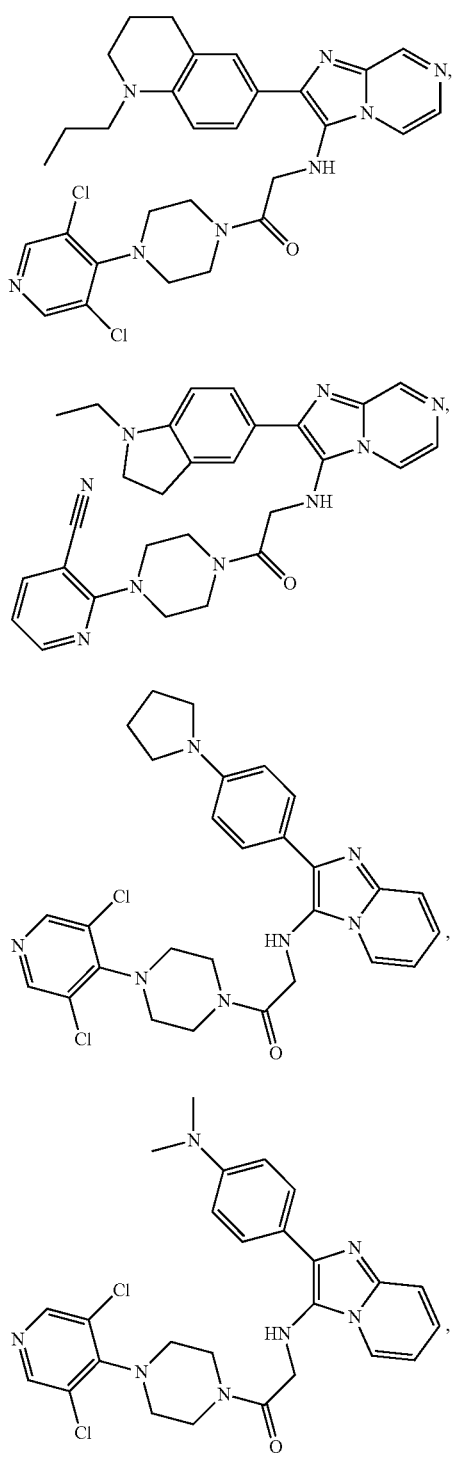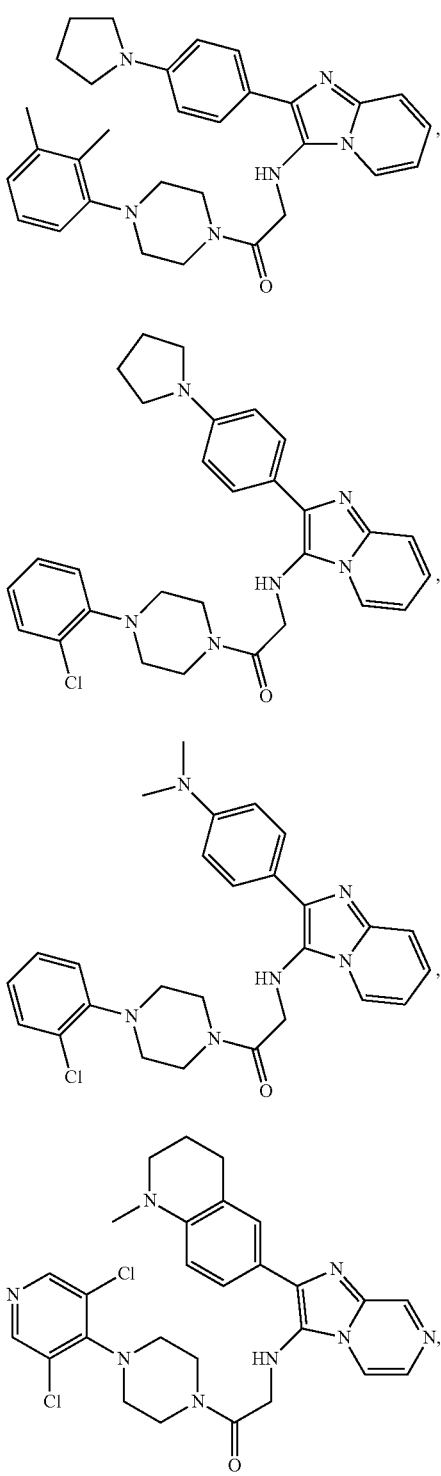

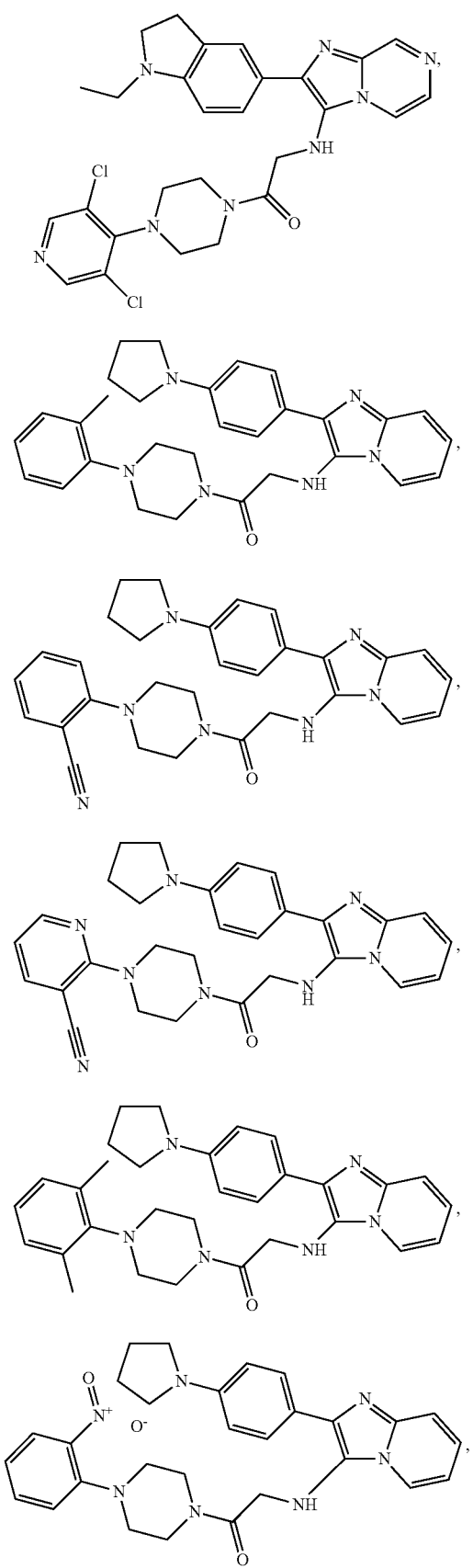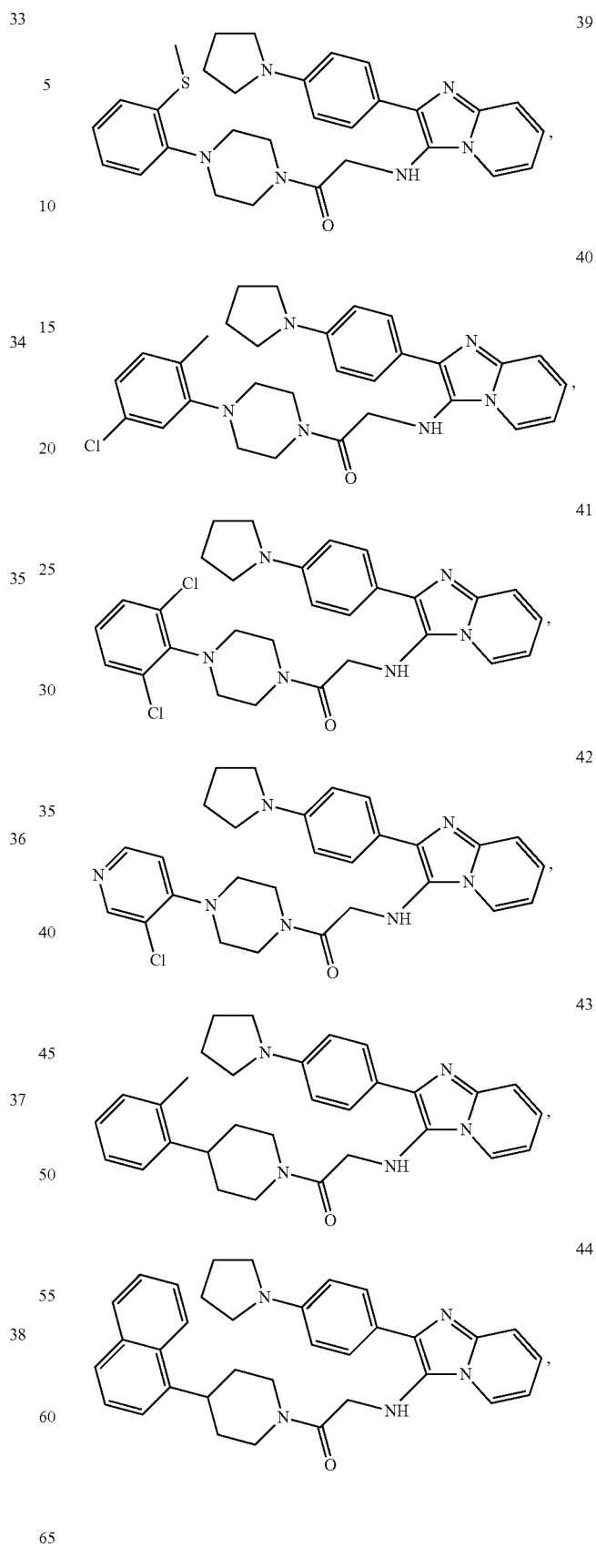

46
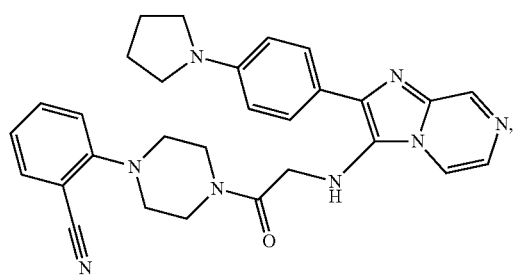
47
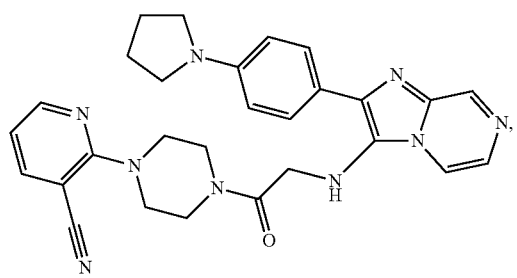
48
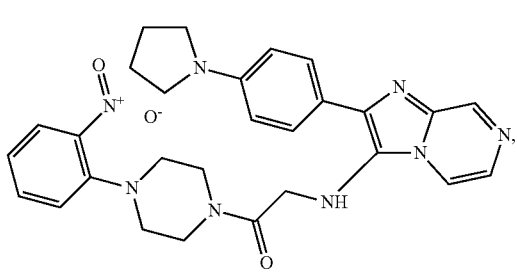
49
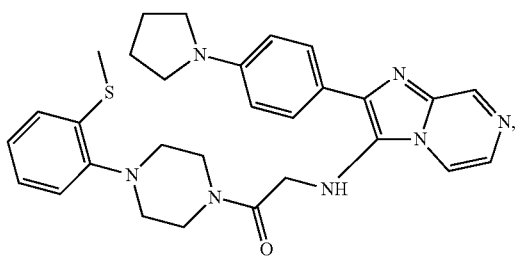
50
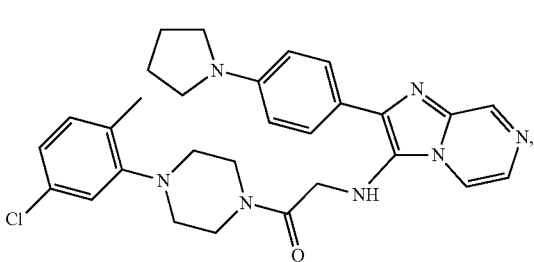
51
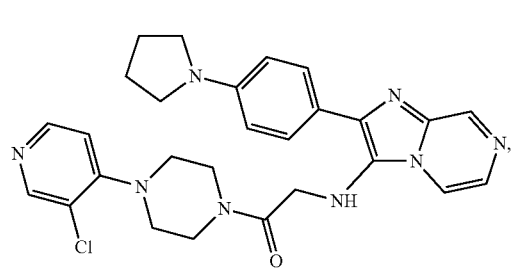
52
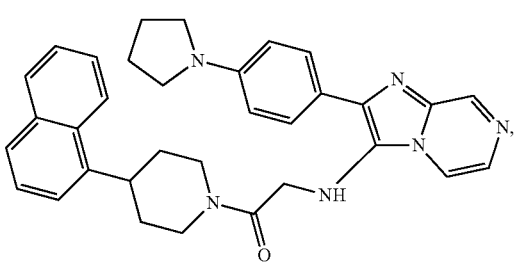
55
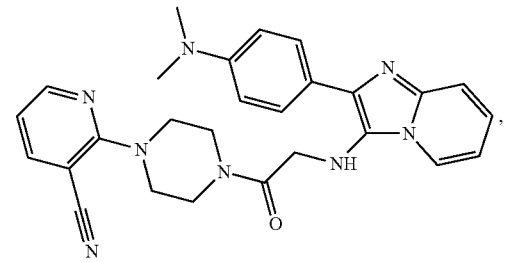
56
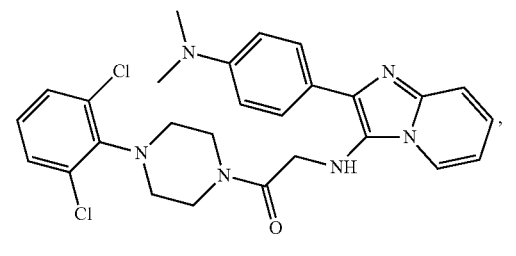
57
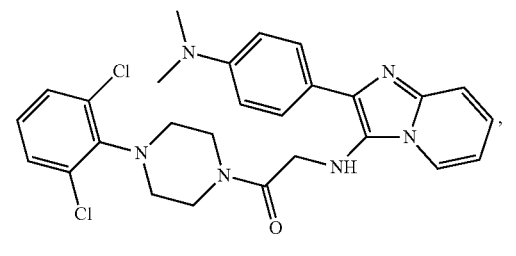
58
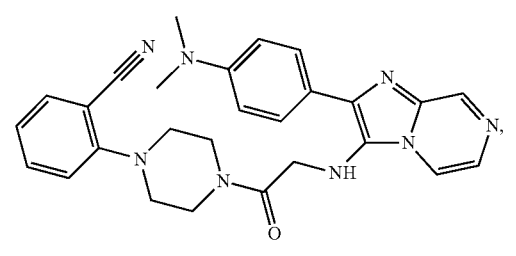
59
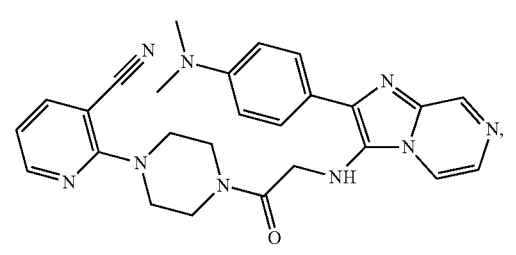

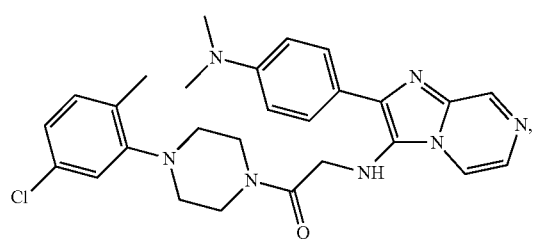
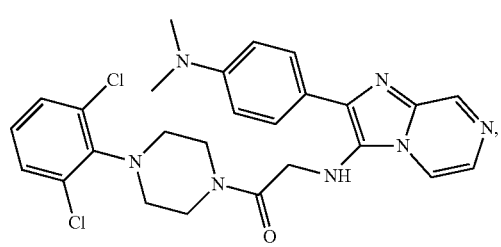
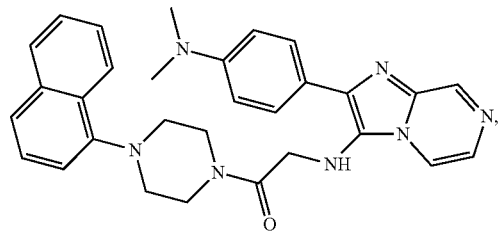
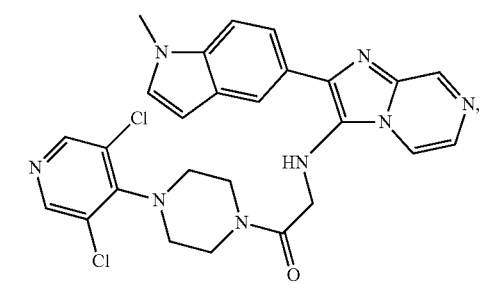
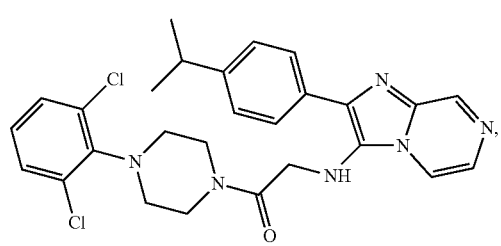
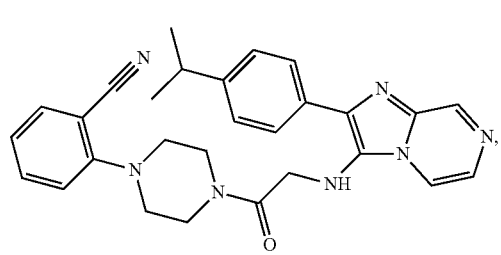
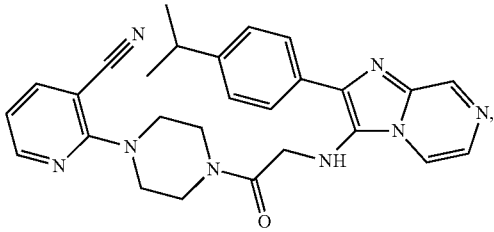
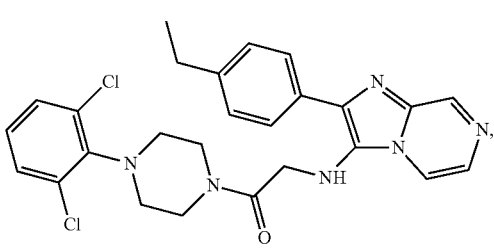
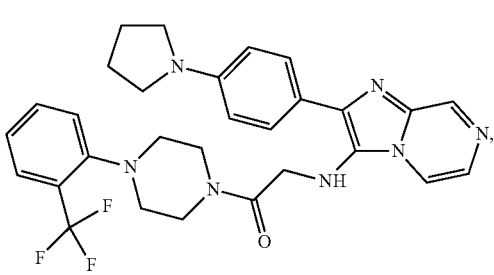
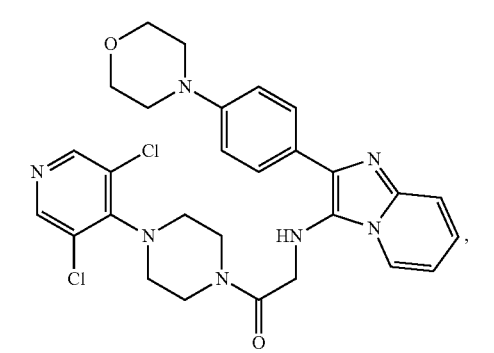
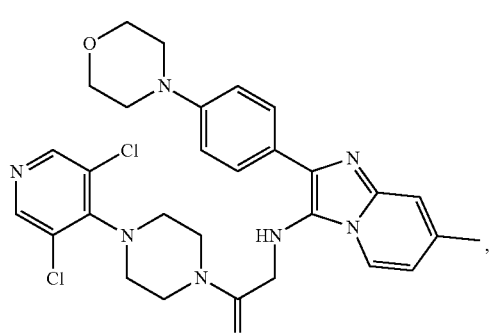

75
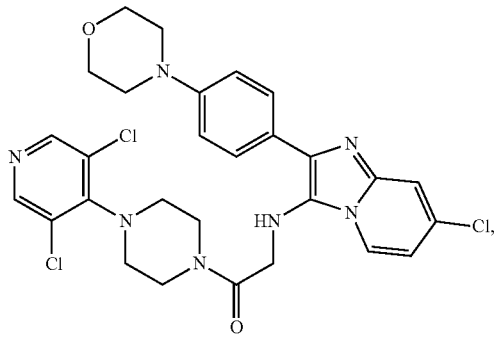
76
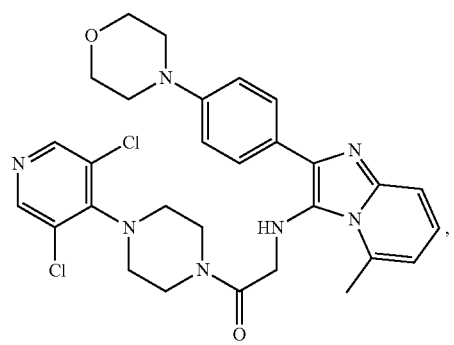
77
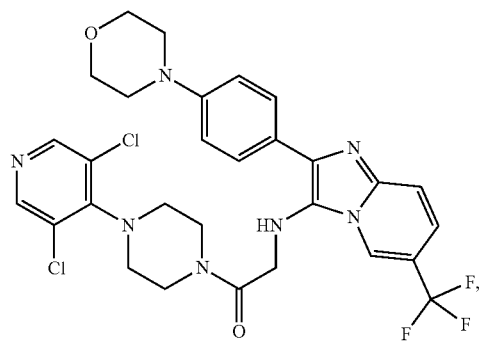
78
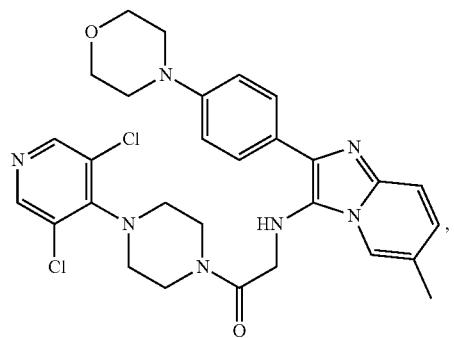
79
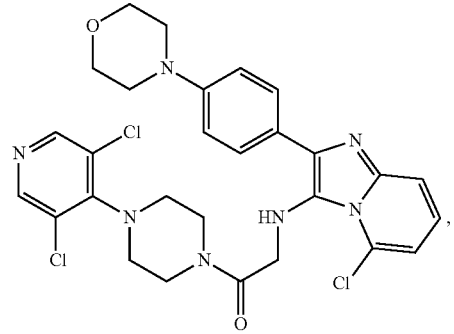
80
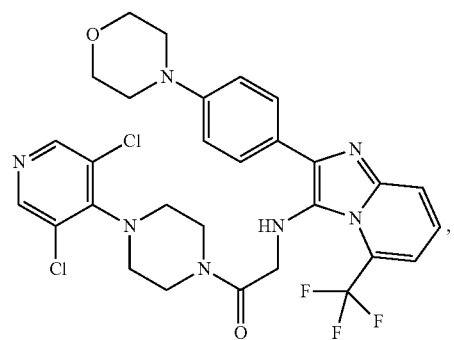
81
82

-continued

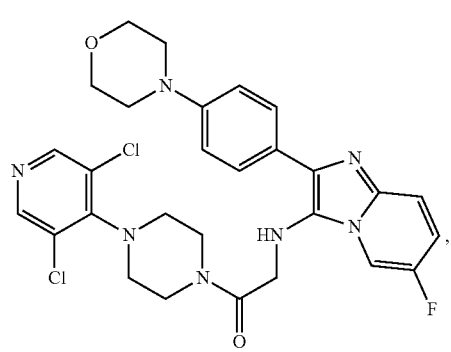
83

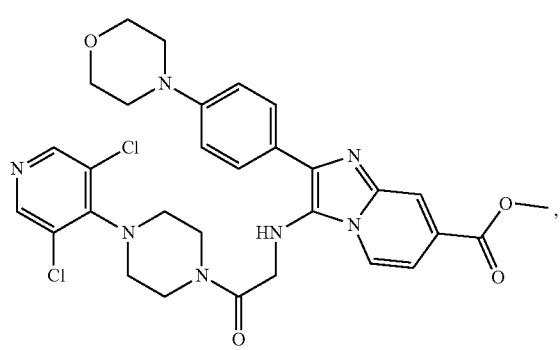
84

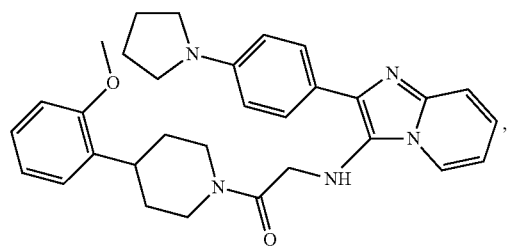
85

-continued

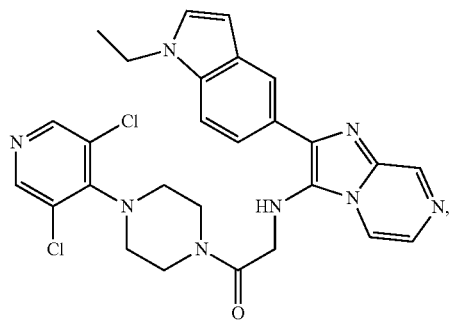
86 or a pharamaceutically acceptable salt thereof.

7. An isolated or purified form of a compound of claim 1, or a pharmaceutically acceptable salt thereof.

8. A pharmaceutical composition comprising a therapeutically effective amount of at least one compound of any of claims 1, or a pharmaceutically acceptable salt thereof, and a pharmaceutically acceptable carrier.

9. A method of treating a bacterial infection, comprising administering to a patient in need of such treatment at least one compound of claim 1, or a pharmaceutically acceptable salt thereof, wherein the bacterial infection is caused by a gram-positive bacterium.

10. The method of claim 9, wherein said bacterial infection is caused by at least one gram-positive bacterium selected from the group consisting of *Bacillus* spp., *Listeria* spp., *Staphylococcus* spp., *Enterococcus* spp., *Clostridium* spp., *Streptococcus* spp., *Actinomyces* spp. and *Mycobacterium* spp.

11. The method of claim 10, wherein said bacterial infection is caused by *Staphylococcus aureus*.

* * * * *